(12) United States Patent
Barbacioru

(10) Patent No.: US 12,100,483 B2
(45) Date of Patent: Sep. 24, 2024

(54) BASE COVERAGE NORMALIZATION AND USE THEREOF IN DETECTING COPY NUMBER VARIATION

(71) Applicant: GRAIL, Inc., Menlo Park, CA (US)

(72) Inventor: Catalin Barbacioru, Fremont, CA (US)

(73) Assignee: GRAIL, LLC, Menlo Park, CA (US)

( * ) Notice: Subject to any disclaimer, the term of this patent is extended or adjusted under 35 U.S.C. 154(b) by 1222 days.

(21) Appl. No.: 15/853,314

(22) Filed: Dec. 22, 2017

(65) Prior Publication Data

US 2018/0225413 A1 Aug. 9, 2018

Related U.S. Application Data

(60) Provisional application No. 62/438,348, filed on Dec. 22, 2016.

(51) Int. Cl.
| | | |
|---|---|---|
| *G16B 30/10* | (2019.01) | |
| *C12Q 1/6869* | (2018.01) | |
| *C12Q 1/6874* | (2018.01) | |
| *C12Q 1/6886* | (2018.01) | |
| *G16B 20/00* | (2019.01) | |
| *G16B 20/20* | (2019.01) | |
| *G16B 30/00* | (2019.01) | |
| *G16B 40/00* | (2019.01) | |

(52) U.S. Cl.
CPC .......... *G16B 30/10* (2019.02); *C12Q 1/6869* (2013.01); *C12Q 1/6874* (2013.01); *C12Q 1/6886* (2013.01); *G16B 20/00* (2019.02); *G16B 20/20* (2019.02); *G16B 30/00* (2019.02); *G16B 40/00* (2019.02); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2010/0228496 A1 | 9/2010 | Leong et al. |
| 2014/0066317 A1 | 3/2014 | Talasaz |
| 2014/0256571 A1 | 9/2014 | Konvicka |
| 2015/0066824 A1 | 3/2015 | Harris et al. |
| 2015/0126377 A1 | 5/2015 | Gnirke et al. |
| 2016/0110497 A1 | 4/2016 | Dzakula et al. |
| 2016/0239604 A1 | 8/2016 | Chudova et al. |
| 2016/0275239 A1 | 9/2016 | Devogelaere et al. |
| 2017/0103162 A1 | 4/2017 | Leong et al. |
| 2017/0220735 A1 | 8/2017 | Duenwald et al. |
| 2017/0362638 A1 | 12/2017 | Chudova et al. |

FOREIGN PATENT DOCUMENTS

| | | |
|---|---|---|
| WO | WO 2010/104893 A2 | 9/2010 |
| WO | WO 2014/040206 A1 | 3/2014 |
| WO | WO 2016/094853 A1 | 6/2016 |
| WO | WO 2017/106768 A1 | 6/2017 |
| WO | WO 2017/136059 A1 | 8/2017 |

OTHER PUBLICATIONS

Swarup et al. (FEBS Letters (2007) vol. 581:795-799).*
Aarthy et al. (Molecular Diag. Ther. (2015) vol. 19:339-350).*
Zhou et al. (Seminars in Oncology (2012) vol. 39:440-448).*
Jung et al. (Clinica Chemica Acta (2010) vol. 411:1611-1624).*
Volik et al. (Mol. Cancer Res (2016) vol. 14 [October]:898-908).*
PCT International Search Report, PCT Application No. PCT/US2017/068305, Apr. 23, 2018, 36 pages.
Sathirapongsasuti, J. F. et al., "Exome Sequencing-Based Copy-Number Variation and Loss of Heterozygosity Detection: ExomeCNV," Bioinformatics, Aug. 9, 2011, pp. 2648-2654, vol. 27, No. 19.
Yoon, S. et al., "Sensitive and Accurate Detection of Copy Number Variants Using Read Depth of Coverage," Genome Research, Aug. 5, 2009, pp. 1586-1592, vol. 19, No. 9.
Venkatraman, E.S. et al., "A Faster Circular Binary Segmentation Algorithm for the Analysis of Array CGH Data," Bioinformatics, Jan. 18, 2007, pp. 657-663, vol. 23, No. 6.
Li, W. et al., "Current Analysis Platforms and Methods for Detecting Copy Number Variation," Physiological Genomics, Nov. 6, 2012, pp. 1-16, vol. 45, No. 1.
Li, W. et al., "Current Analysis Platforms and Methods for Detecting Copy Number Variation—Supplemental Information," Physiological Genomics, Nov. 6, 2012, pp. 1-14.
Pique-Regi, R. et al., "Detecting Changes in DNA Copy Number: Reviewing Signal Processing Techniques," IEEE Signal Processing Magazine, IEEE Service Center, Jan. 2012, pp. 98-107, vol. 29, No. 1.

\* cited by examiner

*Primary Examiner* — Lori A. Clow

(74) *Attorney, Agent, or Firm* — Fenwick & West LLP

(57) ABSTRACT

Gene copy number variations are identified for genes in a targeted gene panel. For each gene, coverage at each base position across the gene is determined. The coverage at each base position can be influenced by the hybridization probes that are used to determine the base level coverage of the base position. The base level coverage for each base position is normalized to account for the characteristics of the hybridization probes. To determine whether a copy number variation exists for a gene, the base level coverage of base positions across the gene for a subject is analyzed to determine whether it deviates from the base level coverage of base positions across the gene for previously analyzed, healthy individuals. If a significant deviation exists, a copy number variation for the gene is called.

22 Claims, 14 Drawing Sheets

BASE COVERAGE NORMALIZATION AND USE THEREOF IN DETECTING COPY NUMBER VARIATION

CROSS REFERENCE TO RELATED APPLICATIONS

This application claims the benefit of Provisional U.S. Application No. 62/438,348, filed Dec. 22, 2016, which is incorporated herein by reference in its entirety.

BACKGROUND

This disclosure generally relates to the detection of alterations in a genome, and more specifically to normalizing calculated base level coverage to more effectively detect CNVs.

Copy number variations (CNVs) play an important role in the etiology of many diseases such as cancers. CNVs include, for example, amplification(s) and deletion(s) of genomic regions. Recent advances in sequencing technologies have enabled the characterization of a variety of genomic features, including CNVs. This has led to the development of bioinformatics approaches to detect CNVs from next-generation sequencing (NGS) data. Current CNV algorithms typically start from coverage of genomic regions (e.g., targeted genomic regions), which limits the ability to identify and correct sources of coverage variation below the region level. There is a need for new methods of detecting CNVs in NGS data (e.g., targeted sequencing data).

SUMMARY

Embodiments described herein relate to methods of analyzing sequencing data to detect CNVs in a nucleic acid sample. Detecting CNVs in a nucleic acid sample obtained from a human subject can be informative for determining a presence of cancer in the subject. In one embodiment, detecting CNVs in a nucleic acid sample obtained from a human subject can be used for early detection of cancer in the subject.

In various embodiments, the methods described herein determines coverage at individual nucleotide bases determined from targeted sequencing reads. Sources of coverage variation can be corrected at the base level. For each gene of a targeted gene panel, the determined base level coverage across bases of the gene can be considered to more effectively detect CNVs of each gene.

Generally, baseline coverage biases that exist at each base position can be modeled using training data gathered from healthy individuals. Therefore, when analyzing a test sample obtained from a subject, the base level coverage can be determined for each base position in view of the expected coverage biases obtained through modeling. Specifically, if the coverage bias at a base position for a test sample obtained from the subject differs from the expected coverage bias obtained through modeling, coverage biases can be normalized and removed. For a gene in a targeted gene panel, base level coverages across the base positions of the gene are analyzed to determine whether the coverage for the gene differs from an expected level of coverage for the gene as previously determined using training data gathered from healthy individuals. If so, a CNV can be called. The calling of a CNV can indicate a presence of cancer in the subject or that the subject is susceptible to an increased likelihood of developing cancer.

DETAILED DESCRIPTION

Figure 1A:
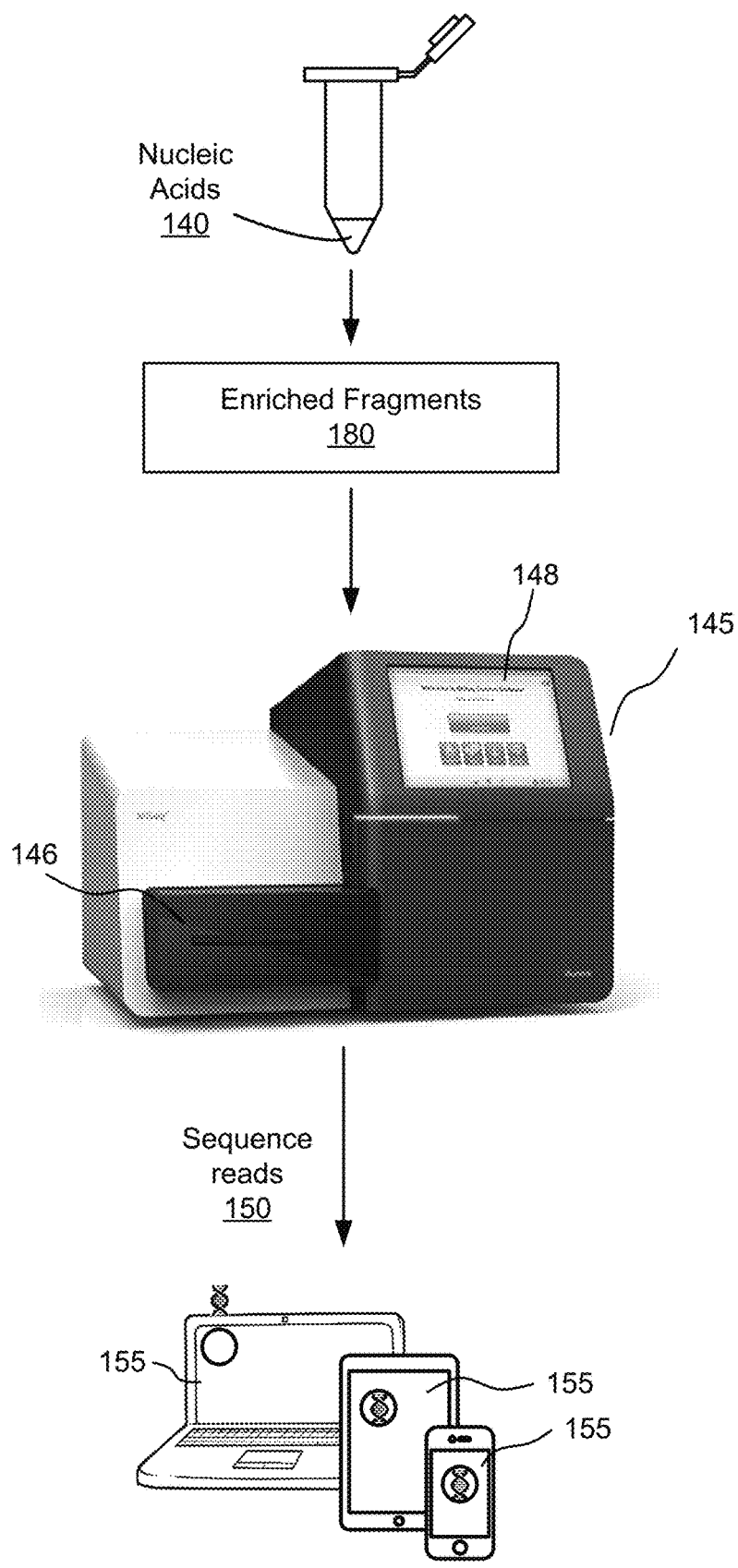
FIG. 1A is an example depiction of the systems used in detecting copy number variations in a test sample, in accordance with an embodiment.

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. For example, a letter after a reference numeral, such as "probe 165A," indicates that the text refers specifically to the element having that particular reference numeral. A reference numeral in the text without a following letter, such as "probe 165," refers to any or all of the elements in the figures bearing that reference numeral (e.g. "probe 165" in the text refers to reference numerals "probe 165A" and/or "probe 165B" in the figures).

The term "individual" refers to a human individual. The term "healthy individual" refers to an individual presumed to not have a cancer or disease. The term "subject" refers to an individual who is known to have, or potentially has, a cancer or disease.

The term "sequence reads" refers to nucleotide sequences read from a sample obtained from an individual. Generally, sequence reads are obtained post-amplification (e.g., polymerase chain reaction such as bridge amplification) of a nucleic acid fragment that is obtained, or pulled-down from a test sample, using a hybridization probe.

The term "cell free nucleic acid," "cell free DNA," or "cfDNA" refers to nucleic acid fragments that circulate in an individual's body (e.g., bloodstream) and originate from one or more healthy cells and/or from one or more cancer cells.

Methods for Identifying Copy Number Variations
General Processing Steps for Identifying Copy Number Variations Figure (FIG. 1A is an example depiction of the systems used in detecting CNVs in a test sample, in accordance with an embodiment. In various embodiments, nucleic acids 140 are isolated from a test sample obtained from a subject (e.g., a patient) and provided to a sequencer 145 for generating sequence reads 150 of the nucleic acids 140. The sequencer 145 is communicatively coupled with one or more computing devices 155. Each computing device 155 can process the sequence reads 150 to determine whether the genome of the subject that the test sample from which the nucleic acids 140 were isolated from includes one or more CNVs.

Referring to FIG. 1A, nucleic acids 140 are isolated from a test sample obtained from a subject (e.g., a patient). In one embodiment, the test sample may be from a patient known to have or suspected of having cancer. The test sample may be a sample selected from the group consisting of blood, plasma, serum, urine, fecal, and saliva samples. Alternatively, the test sample may comprise a sample selected from the group consisting of whole blood, a blood fraction, a tissue biopsy, pleural fluid, pericardial fluid, cerebral spinal fluid, and peritoneal fluid. In accordance with some embodiments, the test sample comprises cell-free nucleic acids (e.g., cell-free DNA), wherein the cell-free nucleic acids in the test sample originate from one or more healthy cells and from one or more cancer cells.

Figure 1B:
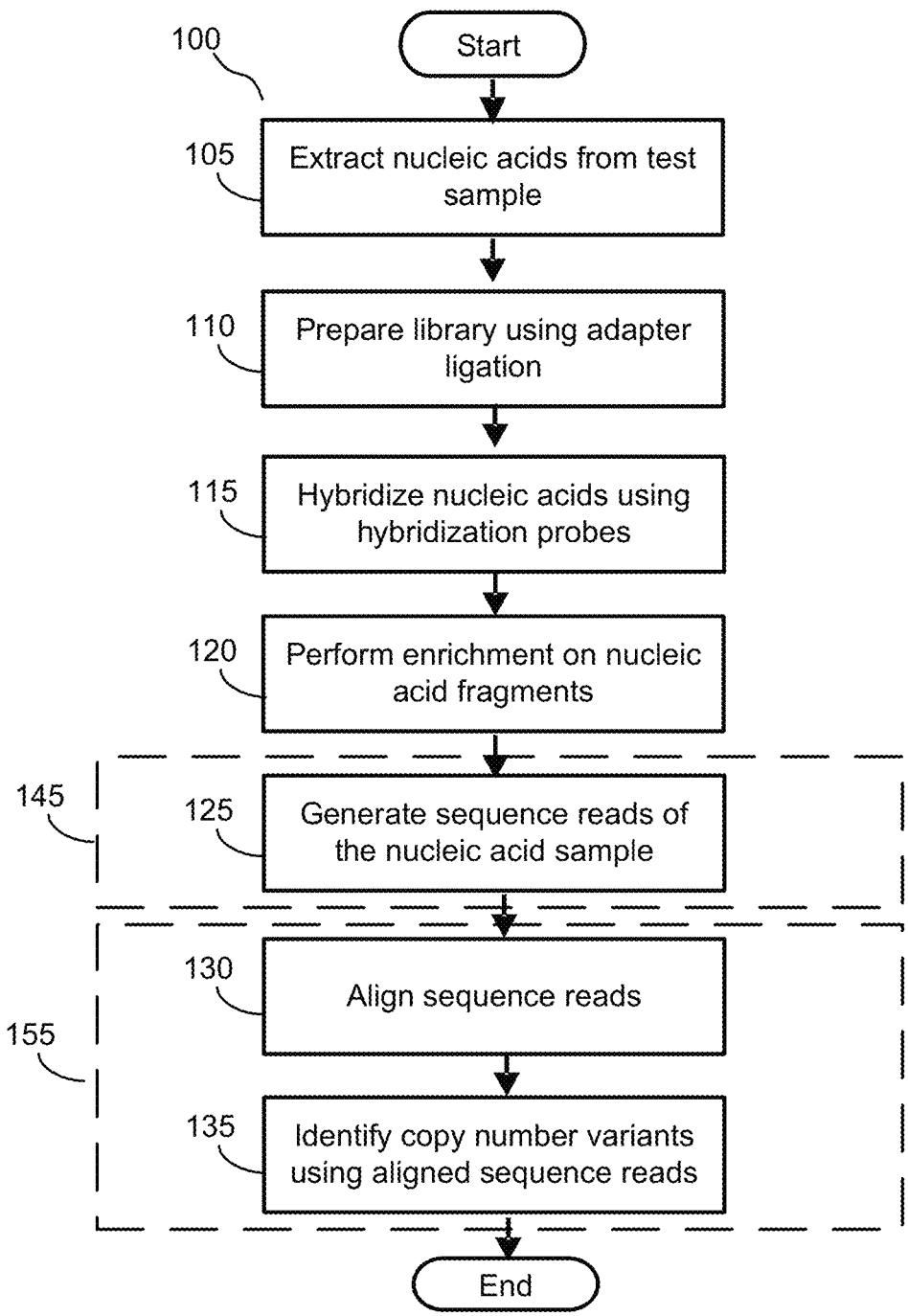
FIG. 1B illustrates a flow diagram of a method for analyzing targeted sequencing data to detect copy number variations in a test sample, e.g., for a cell-free DNA (cfDNA) sample, in accordance with an embodiment.

In various embodiments, the nucleic acids 140 undergo enrichment to generate enriched fragments 180. As described below in reference to FIG. 1B, generating enriched fragments includes hybridizing the nucleic acids 140 using hybridization probes and enriching the probe-nucleic acid complex. The enriched fragments 180 are provided to the sequencer 145 for sequencing. Examples of a sequencer 145 for sequencing the enriched fragments 180 from a test sample include the Illumina HiSeq™ or Illumina MiSeq™ Systems. As shown in FIG. 1B, the sequencer 145 can include a graphical user interface 148 that enables user interactions with particular tasks (e.g., initiate sequencing, terminate sequencing) as well as one more loading trays 146 for providing the enriched fragment 180 samples and/or necessary buffers for performing the sequencing assays. Therefore, once a user has provided the necessary reagents and enriched fragment 180 samples to the loading trays 146 of the sequencer 145, the user can initiate sequencing by interacting with the graphical user interface 148 of the sequencer 145. The sequencer 145 performs the sequencing and outputs sequence reads 150 of the enriched fragments 180 from the test sample.

Each computing device 155 can be one of a personal computer (PC), a desktop computer, a laptop computer, a notebook, a tablet PC, a mobile device. A computing device 155 can be communicatively coupled to the sequencer 145 through a wireless, wired, or a combination of wireless and wired communication technologies. Generally, the computing device 155 is configured with a processor and memory storing computer instructions that, when executed by the processor, cause the processor to process the sequence reads 150 and determine the presence of CNVs in the genome of a subject from whom the test sample was obtained.

Reference is now made to FIG. 1B, which illustrates a flow diagram of the method 100 for detecting CNVs in a test sample, in accordance with an embodiment. At step 105, nucleic acids 140 are extracted from a test sample. In various embodiments, the test sample is a cfDNA sample obtained from the subject. DNA (e.g., cfDNA) is purified from the test sample. In general, any known method in the art can be used for purifying DNA. For example, nucleic acids 140 can be isolated by pelleting and/or precipitating the nucleic acids 140 in a tube.

At step 110, a sequencing library is prepared. During library preparation, unique molecular identifiers (UMI) are added to the nucleic acids 140 (e.g., DNA or RNA) through adapter ligation. The UMIs are short nucleic acid sequences (e.g., 4-10 base pairs) that are added to ends of nucleic acids 140 during adapter ligation. In some embodiments, UMIs are degenerate base pairs that serve as a unique tag that can be used to identify sequence reads obtained from a nucleic acids. As described later, the UMIs can be further replicated along with the attached nucleic acids during amplification, which provides a way to identify sequence reads that originate from the same original nucleic acid segment in downstream analysis.

After step 110, in various embodiments, one or more of the steps 115, 120 and 125 are performed by individual hardware devices. For example, a first dedicated device can be used for enrichment 120 of targeted nucleic acids (e.g., informative cell-free DNA fragments).

Hybridization probes are hybridized 115 to a set of targeted nucleic acids. The probe-nucleic acid complexes can then be enriched 120 from the sample. For example, as is well known in the art, a biotin moiety can be added to the 5'-end of the probes (i.e., biotinylated) to facilitate pulling down of target probe-nucleic acids complexes using a streptavidin-coated surface (e.g., streptavidin-coated beads). Optionally, a second device, such as a polymerase chain reaction (PCR) device, can be used for amplification of the targeted nucleic acids.

Figure 1C:
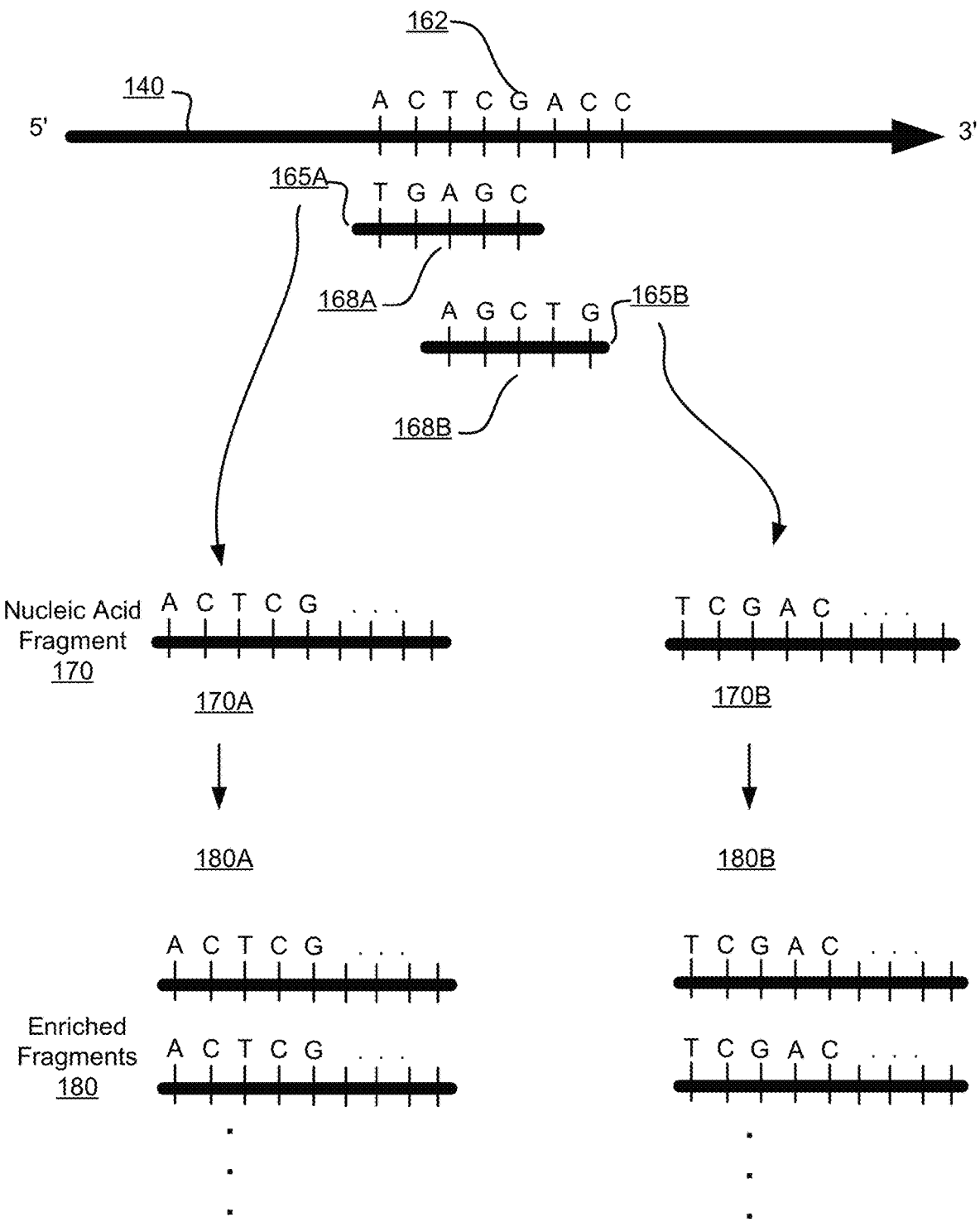
FIG. 1C is a depiction of the processing steps for generating sequence reads of a nucleic acid sample, in accordance with an embodiment.

At step 120, hybridized probe-nucleic acid complexes (from step 115) pulled down from the sample are enriched. Referring to FIG. 1C, it depicts the processing steps for generating sequence reads of a nucleic acid 140, in accordance with an embodiment. Here, for illustrative purposes, the nucleic acid 140 can have a nucleic acid sequence of "ACTCGACC." Each nucleotide in the nucleic acid 140 is hereafter referred to as a base position 162. Hybridization probes 165A and 165B can be designed to target and hybridize with the targeted nucleic acid sequence of the nucleic acid 140 to pull down, and enrich, nucleic acid fragments 170 that may be informative for the presence or absence of cancer (or disease), cancer status, or a cancer classification (e.g., cancer type or tissue of origin). In accordance with this step, a plurality of hybridization pull down probes can be used for a given target sequence or gene. The probes can range in length from about 40 to about 160 bp, from about 60 to about 120 bp, or from about 70 bp to about 100 bp. In one embodiment, the probes cover overlapping portions of the target region or gene.

Probe 165A includes a nucleotide sequence (e.g., "TGAGC") that is complementary to a portion of the nucleotide sequence of the targeted nucleic acid 140 (e.g., "ACTCG"). Additionally, probe 165B includes a nucleotide sequence (e.g., "AGCTG") that is complementary to a portion of the targeted nucleotide sequence of the nucleic acid 140 (e.g., "TCGAC"). Together, probe 165A and probe 165B cover overlapping base positions 162 on the nucleic acid 140 (e.g. "TCG"). Each probe 165A and 165B may include a center position 168A and 168B. The nucleic acid 140 targeted for enrichment with probes 165A and 165B can be used to detect CNVs that may be informative for cancer, which is described in further detail below in relation to FIG. 2.

In one embodiment, each of the probes are designed based on a targeted gene panel to analyze particular mutations or target regions of the genome (e.g., of the human or another organism) that are believed to be informative for certain cancers or other types of diseases. By using a targeted gene panel rather than sequencing all expressed genes of a genome, also known as "whole exome sequencing," the method can decrease sequencing requirements, or allow for increased sequencing depth, of the target regions.

As shown in FIG. 1C, each probe 165A and 165B can be used to pull down nucleic acid fragments 170 to which they hybridize. For example, each of probe 165A or 165B hybridizes with a portion of the nucleotide sequence of the nucleic acid 140 (e.g., 165A hybridizes with "ACTCG") and can be enriched. For example, as previously described, a biotin moiety can be added to the probe to facilitate pulling down of targeted probe-nucleic acids complexes using streptavidin-coated beads. Optionally, the enriched nucleic acids can be amplified (e.g., using PCR) prior to sequencing.

At step 125, the enriched fragments 180 are sequenced by the sequencer 145 to generate sequence reads 150. Sequence reads 150 may be acquired by known means in the art. For example, step 125 may employ next generation sequencing (NGS) techniques including synthesis technology, pyrosequencing, ion semiconductor technology, single-molecule real-time sequencing, sequencing by ligation, nanopore sequencing, or paired-end sequencing. In some embodiments, massively parallel sequencing is performed using sequencing-by-synthesis with reversible dye terminators. The sequence reads 150 can be provided by the sequencer 145 to the computing device 155 for further analysis. In various embodiments, the sequence reads 150 are provided to the computing device 155 as a BAM file.

As shown in FIG. 1B, the computing device 155 may perform steps 130 and 135 to identify CNVs. At step 130, sequence reads are obtained and aligned to a reference genome. In general, any known method in the art can be used for aligning the sequence reads to a reference genome. For example, the nucleotide bases of a sequence read are aligned with nucleotide bases in the reference genome to determine alignment position information for the sequence read. Alignment position information can include a beginning position and an end position of a region in the reference genome that corresponds to the beginning nucleotide base and end nucleotide base of the sequence read. Alignment position information may also include sequence read length, which can be determined from the beginning position and end position. In various embodiments, a BAM file of aligned sequencing reads for regions of the genome is obtained and utilized for analysis in step 135.

At step 135, CNVs are identified using the aligned sequence reads. Generally, CNVs are determined for a targeted gene panel to analyze particular mutations or target regions of the genome. For each gene in the targeted gene panel, coverage at each base position is determined. The coverage at each base position can be susceptible to various biases of that base position such as characteristics of the one or more hybridization probes that were used to determine the base level coverage of the base position, GC content around the base position, and mappability of the base position. The base level coverage for each base position is normalized to account for the various biases. To determine whether a CNV likely exists for a gene, the base level coverage of base positions across the gene for a subject is analyzed to determine whether it deviates from the base level coverage of base positions across the gene for previously analyzed, healthy individuals. If a significant deviation exists, then the gene of the subject likely includes one or more CNVs. The process for identifying CNVs is described in further detail below in reference to FIGS. 2, 3A, and 3B.

Generating Models for Identifying Copy Number Variations

Figure 2:
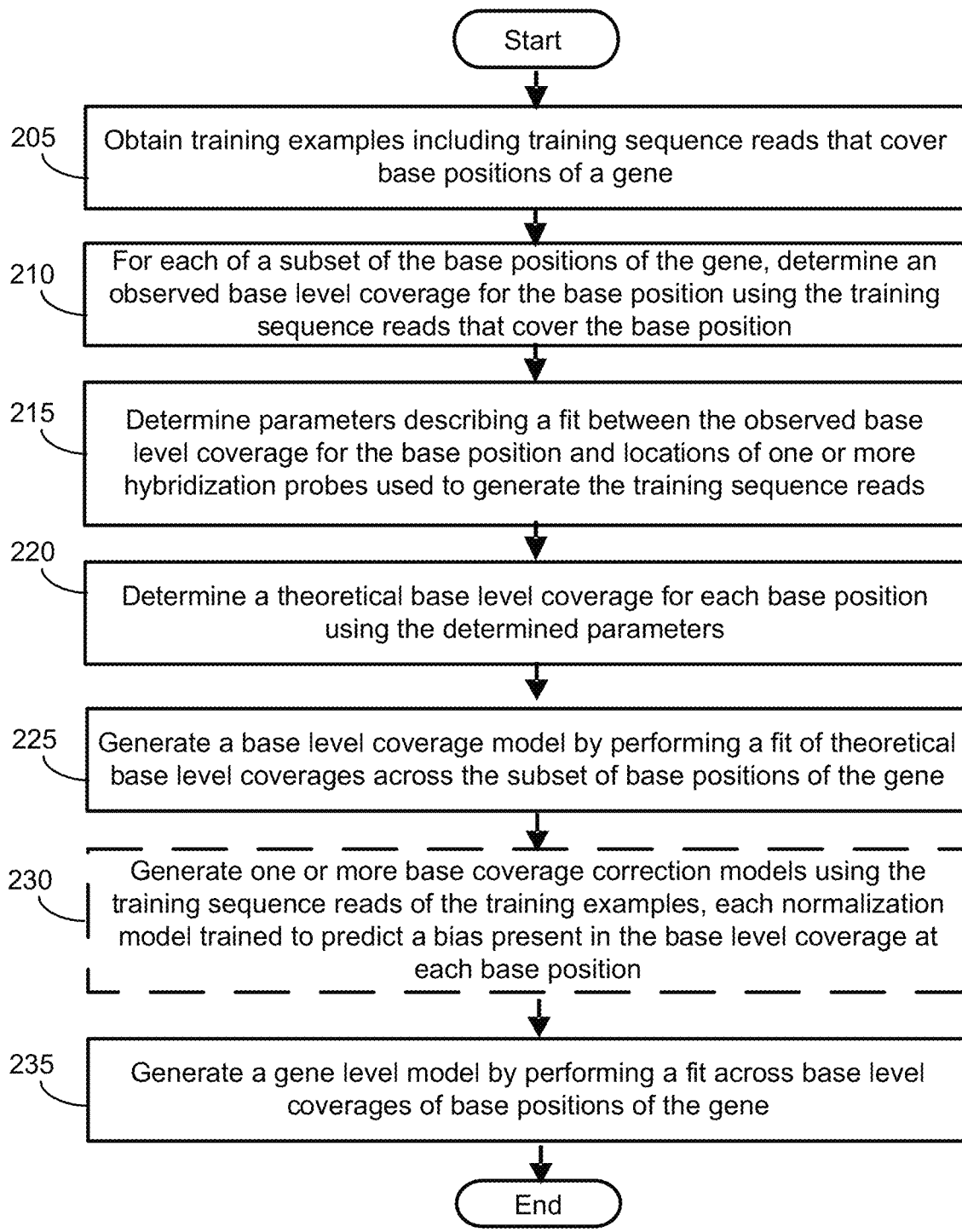
FIG. 2 is a flow process for generating models that are applied during deployment for detecting a copy number variation, in accordance with an embodiment.

FIG. 2 is a flow process for generating models that are applied during deployment for detecting a CNV, in accordance with an embodiment. A first model, hereafter referred to as a base level coverage model predicts a base level coverage for each base position of a gene. Here, in determining each base level coverage, the base level coverage model takes into consideration the characteristics of one or more probes that are used to pull down a targeted nucleic acid and generate a sequence read that covers the base position. A second model, hereafter referred to as a gene level model, determines a likelihood of a CNV of a gene. Here, the gene level model considers the base level coverage across base positions of the gene to determine whether the coverage level across the gene differs from an expected level of coverage of the gene. A significant difference indicates a likely presence of a CNV. In various implementations of this or other embodiments, one or more additional models, hereafter referred to as base coverage correction models, determine whether an unexpected bias exists for a base position in the genome. Examples of bias can arise from guanine-cytosine content, mappability, general variability, or other unexplained sources. The base coverage correction models may include, but are not limited to, a GC content model, a mappability model, a principal component analysis model, and a base filtering model.

Referring to FIG. 2, at step 205, training examples are obtained. Each training example includes training sequence reads that cover base positions of a gene. Training sequence reads from training examples can be derived from a single healthy individual or a plurality of healthy individuals. Training sequence reads can be obtained according to the steps of 105-130 shown in FIG. 1A.

The subsequent description refers to observed or theoretical base level coverage and scaled base level coverage. For notation purposes, observed base level coverage for a base position is denoted as $B^o(i)$ and theoretical base level coverage for a base position is denoted as $B^t(i)$. Additionally, observed scaled base level coverage is denoted as $s^o(i)$ and theoretical scaled base level coverage is denoted as $s^t(i)$.

At step 210, an observed base level coverage $B^o(i)$ for each base position i of the gene is determined using the training sequence reads. In various embodiments, an observed base level coverage $B^o(i)$ for each of a subset of base positions of the gene is determined. The observed base level coverage $B^o(i)$ for a base position of the gene is the total number of training sequence reads derived from one or more healthy individuals that cover the base position of the gene. Given that healthy individuals are unlikely to have CNVs of genes, the observed base level coverages $B^o(i)$ of the training sequence reads at each base position can serve as a baseline for determining whether CNVs exist in possible subjects that may be at risk for having or developing cancer.

At step 215, for each of the subset of the base positions of the gene, a fit between the observed base level coverage $B^o(i)$ at the position and locations of hybridization probes used to generate the training sequence reads is performed. To provide an example of the location of hybridization probes, reference is made to FIG. 1C. Assume that the guanine nucleotide base 162 on the nucleic acid 140 is the target base position i for which the fit is being performed. Each probe 165 that hybridizes with bases of the nucleic acid 140 can have a genomic position $p_c$. The genomic position $p_c$ of a probe 165 is defined as the position in the genome that aligns with the center position 168 of the probe 165. For probe 165A, the genomic position $p_c$ of the probe 165A refers to the adenine nucleotide base 168A that is the center nucleotide base of the probe 165A. Here, the genomic position $p_c$ of the probe 165A is two nucleotide bases away from the target base position i of the guanine nucleotide base 162. Similarly, for probe 165B, the genomic position $p_c$ of the probe 165B refers to the cytosine nucleotide base 168B that is the center nucleotide base of the probe 165B. Here, the genomic position $p_c$ of the probe 165B matches the target base position i of the guanine nucleotide base 162.

For a probe centered at a genomic coordinate $p_c$, the base level coverage B(i), where the base level coverage is the number of reads overlapping a given position, of the base at position i can generally be represented by a second degree equation:

$$B(i)=\alpha-\beta^*(i-p_c)^2 \quad (1)$$

where $\alpha$ and $\beta$ are parameters. This second degree equation reflects the fact that a probe with a genomic position $p_c$ that is near the target base position i heavily contributes to the base level coverage B(i) in comparison to a different probe with a genomic position $p_c$ that is further from the target base position i. To determine the parameters $\alpha$ and $\beta$ for a base position, B(i) in equation (1) can be replaced with the observed base level coverage $B^o(i)$ for the base position derived from training sequence reads derived from different healthy individuals.

The value of coefficient $\alpha$ is based, for example, on the overall coverage level of sample coverage and can be considered a constant across all probes. For known values of $\beta$ coefficients, a linear model can be used across all probes and base positions to estimate coefficient $\alpha$.

The value of the $\beta$ coefficient for a probe is based, for example, on the pull-down efficiency of the probe that hybridized with bases within the region of the gene. Probe pull-down efficiency can be determined, for example, based on the guanine-cytosine (GC) content of the probe. Because of their GC content, different probes may have different efficiencies in pulling down a DNA fragment. For example, if a probe has a very high GC content, or a very low GC content, the efficiency in pulling down a DNA fragment is generally low. If a probe has roughly a 50% GC content and 50% AT content then the efficiency is typically higher than probes having higher or lower levels of GC content. In other words, a probe that is more balanced in GC content is more efficient at pulling down DNA fragments than a probe that has extreme values of GC content.

Equation 1 depicts a fit between base coverage B(i) of a base position and the genomic coordinate of a single probe. For a base position where n probes cover the base position, the fit between base coverage B(i) of the base position and the genomic coordinate $p_{Cn}$ of each of the probes can be expressed as:

$$B(i)=\Sigma_1^n(\alpha_n-\beta_n(i-p_{cn})^2 \quad (2)$$

In words, the base level coverage B(i) for base position i can be a summation of the individual base level coverages contributed by each probe, where the fit produces parameters ($\alpha_n$ and $\beta_n$) for each probe. To solve for $\alpha_n$ and $\beta_n$, the observed base level coverage $B^o(i)$ at each base position determined using training sequence reads is used in Equation (2) in place of the general base level coverage B(i).

At step 220, theoretical base level coverage $B^t(i)$ is determined for each base position using the $\alpha_n$ and $\beta_n$ parameters. Here, the theoretical base level coverage $B^t(i)$ represents the modeled base level coverage for each base position. Referring to Equation (2), the parameters $\alpha_n$ and $\beta_n$ are now known. Given each probe genomic position $p_c$ yields a theoretical base level coverage $B^t(i)$ at each base position i.

At step 225, the base level coverage model is generated by performing a fit of theoretical base level coverage $B^t(i)$ across base positions of the gene to obtain parameters of the base level model. In various embodiments, the base level coverage model performs a fit of theoretical base level coverage $B^t(i)$ across a region of the gene, the region of the gene including one or more base positions. Therefore, for a single gene, different parameters of the base level coverage model are determined for each of multiple regions of the gene.

Generally, the base level coverage model describes a relationship between scaled base level coverage s(i) across the base positions of the region of the gene and base level coverage B(i). In one embodiment, the base level coverage model is a robust linear fit. For example, a general linear fit can be expressed as:

$$s(i)=x+y^*B(i)+\text{error} \quad (3)$$

where x and y are the parameters of the base level coverage model and error is a variability term.

To determine the parameters of the base level coverage model, an observed scaled base level coverage $s^o(i)$ for each base position is determined using the observed base level coverage $B^o(i)$ obtained using the training sequence reads. The observed base level coverage for each base position is scaled to the median base level coverage that was observed across the entire sample obtained from a healthy individual. Scaling allows coverages of training sequences derived from different samples to be comparable. For example, in one embodiment, the scaled base level coverage $s^o(i)$ for each base position is determined by dividing the observed base level coverage $B^o(i)$ by the median base coverage determined for the test sample. Given the theoretical base level coverage $B^t(i)$ and observed scaled base level coverage $s^o(i)$, Equation (3) can be expressed as:

$$s^o(i)=x+y^*B^t(i)+\text{error} \quad (4)$$

The parameters x and y can be determined using Equation (4). The parameters of the base level coverage model (e.g., x and y) can be stored and subsequently retrieved during deployment for use in determining the presence of a CNV in a sample.

At step 230, one or more base coverage correction models are trained using the training sequence reads of the training examples. Each base coverage correction model considers a level of bias present in the base level coverage at each base position. In various embodiments, base coverage correction models include one or more of a GC content model, a mappability model, a principal component analysis model, and a base filtering model.

The GC content model predicts a GC bias for a base position based on the level of GC content within a window of the region of the gene. The base position is centered within the window. In various embodiments, the size of the window is dependent on the size of the probe or the size of a nucleic acid fragment 170. For example, the size of the window may be larger than the size of the probe or may be larger than the size of the nucleic acid fragment 170. In various embodiments, the window of the region of the gene is between 4 and 200 base pairs. In various embodiments, the window of the region of the gene is between 5 and 100 base pairs in size. In various embodiments, the window of the region of the gene is between 6 and 80 base pairs in size. In various embodiments, the window of the region of the gene is between 6 and 80 base pairs in size. In one embodiment, the window of the region of the gene is between 8 and 60 base pairs in size, or any sub-range therein. In another embodiment, the window of the region of the gene is between 10 and 40 base pairs in size. In another embodiment, the window of the region of the gene is between 12 and 30 base pairs in size. In another embodiment, the window of the region of the gene is at least 5 base pairs in size. In another embodiment, the window of the region of the gene is at least 10 base pairs in size. In another embodiment, the window of the region of the gene is at least 15 base pairs in size. In another embodiment, the window of the region of the gene is at least 20 base pairs in size. In another embodiment, the window of the region of the gene is at least 25 base pairs in size. In another embodiment, the window of the region of the gene is 21 base pairs in size. In another embodiment, for a base position, the window includes the ten bases to the left and to the right of the base position.

The GC content model predicts a GC content for a window around the base position by approximating a smoothing function across the GC content of base positions in the window. In one embodiment, the smoothing function is a local polynomial regression (LOESS) curve fit that smoothes the GC content across the window. Therefore, the GC content model can output a GC content value by using the approximated smoothing function.

By providing training sequence reads derived from various healthy individuals as input to the GC content model, the GC content model approximates the smoothed function and predicts a baseline GC content for each base position using the smoothed function. Here, the baseline GC content for a base position is the GC content in a window around the base position. The predicted baseline GC content for each base position is stored such that during deployment, the baseline GC content for each base position can be used to determine whether an additional GC correction needs to be performed.

The mappability model predicts a mappability bias for a base position based on the mappability of each base position within a window of the region of the gene. Similar to the window described above in reference to the GC content model, the window of the region of the gene used to predict a mappability bias for a base position can be any of the aforementioned sizes. In particular embodiments, the window of the region of the gene used to predict a mappability bias for a base position is 21 base pairs in size The mappability for each base position can be accessed from publicly available databases such as the UC Santa Cruz Genome Browser. The mappability model predicts a mappability bias for a base position by approximating a smoothed function across the mappability of base positions in the window. In one embodiment, the smoothing function is a local polynomial regression (LOESS) curve fit that smoothes the mappability levels of base positions within the window. The mappability model outputs a mappability for the base position by using the approximated smoothed function. By providing training sequence reads derived from various healthy individuals, the mappability model predicts a baseline mappability for each base position. The baseline mappability for each base position can be used during deployment to determine whether an additional mappability correction needs to be performed.

The principal component analysis model predicts biases for each base position that can arise from unknown sources. Given training sequence reads, the principal component analysis model performs a principal component analysis (PCA) to identify principal components $PC_n$ for each observed scaled base level coverage $s^o(i)$ for each base position i. The PCA analysis can be expressed as:

$$s^o(i) = a + b_1 * PC_1(i) + \ldots + b_n * PC_n(i) \qquad (5)$$

Here, each of the parameters (a, $b_1 \ldots b_n$) and the principal components $PC_n$ are determined using the observed scaled base level coverage $s^o(i)$ derived from the training examples. These principal components represent the baseline such that during deployment, the principal component analysis model can be applied to determine whether the PCA analysis yields additional unknown biases that differ from the baseline.

The base filtering model determines statistical measures of the observed scaled base level coverage $s^o(i)$ for the base position i. For example, the base filtering model receives, as input, the observed scaled base level coverage $s^o(i)$ for each base position and calculates a median base level coverage for each base position and a standard deviation of the base level coverage for each base position. The median and standard deviation of the base level coverage for each base position can serve as a baseline for determining whether a scaled base level coverage determined during deployment is a significant outlier. If $s^o$, the scaled base level coverage for the base position can be filtered and removed.

Returning to FIG. 2, at step 235, a gene level model is generated by performing a fit of base level coverage of positions across multiple regions of the gene to obtain parameters of the gene level model. In one embodiment, the gene level model is a robust linear model and can be expressed as:

$$f(i) = a + m*i + \text{error} \qquad (6)$$

where f(i) can be either the scaled observed base level coverage $s^o(i)$ or the observed normalized base level coverage z(i) that is obtained output from the z-score model. Here, a is the parameter learned across the training examples and m is the slope of the linear fit, otherwise referred to as the gene coefficient for the gene. The gene level model outputs the gene coefficient for the gene, which can be used to make inferences about the amplification or deletion of regions of the gene.

The gene level model can include multiple linear fits, where each linear fit is specific for a gene in the targeted gene panel. Therefore, for each of n different genes in the targeted gene panel, each linear fit of the gene level model can be expressed as:

$$f_n(i) = a_n + m_n * i + \text{error} \quad (7)$$

Thus, the gene level model can output each gene coefficient $m_n$ for each gene in the targeted gene panel to determine the likelihood of a CNV (e.g., duplication or deletion) of a region of the gene.

Identifying Copy Number Variations in a Test Sample

Figure 3A:
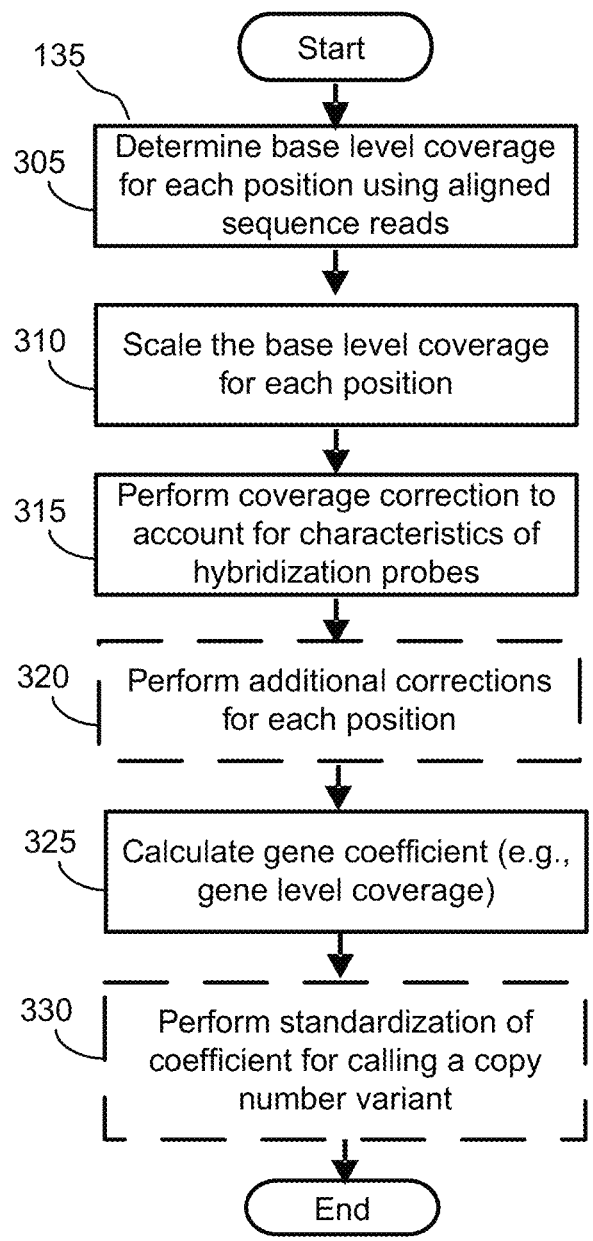
FIG. 3A is a flow diagram of a method for normalizing calculated coverage for identification of copy number variations, in accordance with an embodiment.

FIG. 3A is a flow diagram of a method for identifying CNVs in a test sample, in accordance with an embodiment. The test sample is processed using the process workflow described in FIG. 1A. Specifically, the aligned sequence reads of the test sample are generated using processing steps 105-130. FIG. 3A describes step 135 in further detail.

At step 305, the base level coverage for each position in a region of a gene is determined from the aligned sequencing reads that each cover the position. In general, any known method in the art can be used to determine base level coverage. Here, the number of sequence reads overlapping a given base position represents the base level coverage for that base position. As used hereafter, the notation $B^d(i)$ refers to the base level coverage determined, during deployment, for each base position for a target sample obtained from a subject. Additionally, the notation $s^d(i)$ refers to the scaled base level coverage determined, during deployment, for each base for the target sample obtained from a subject.

At step 310, the base level coverage $B^d(i)$ is scaled to the median coverage that was observed within the entire sample. For example, in one embodiment, the scaled base coverage is determined by dividing the base level coverage by the median base coverage determined for the test sample. Scaling allows coverages from different samples to be compared.

At step 315, the base level coverage $B^d(i)$ for each base position is corrected to account for characteristics of the hybridization probes that were used to obtain the nucleic acid fragments (e.g., nucleic acid fragments 170) that were subsequently used to generate the sequence reads. For example, the base level coverage model is retrieved and the base level coverage for each base position within a region of the gene is applied as input to the base level coverage model to determine the scaled base level coverage of each base position. The scaled base level coverage $s^d(i)$ of each base position i can be determined using the fit expressed as:

$$s^d(i) = x + y * B^d(i) + \text{error} \quad (8)$$

where the parameters x and y were previously trained using the training examples and $B_d(i)$ is the base level coverage at base position i. Examples of scaled base coverage across various regions of a gene determined using the base level coverage model are described in further detail below with reference to FIGS. 7 and 8.

Figure 3B:
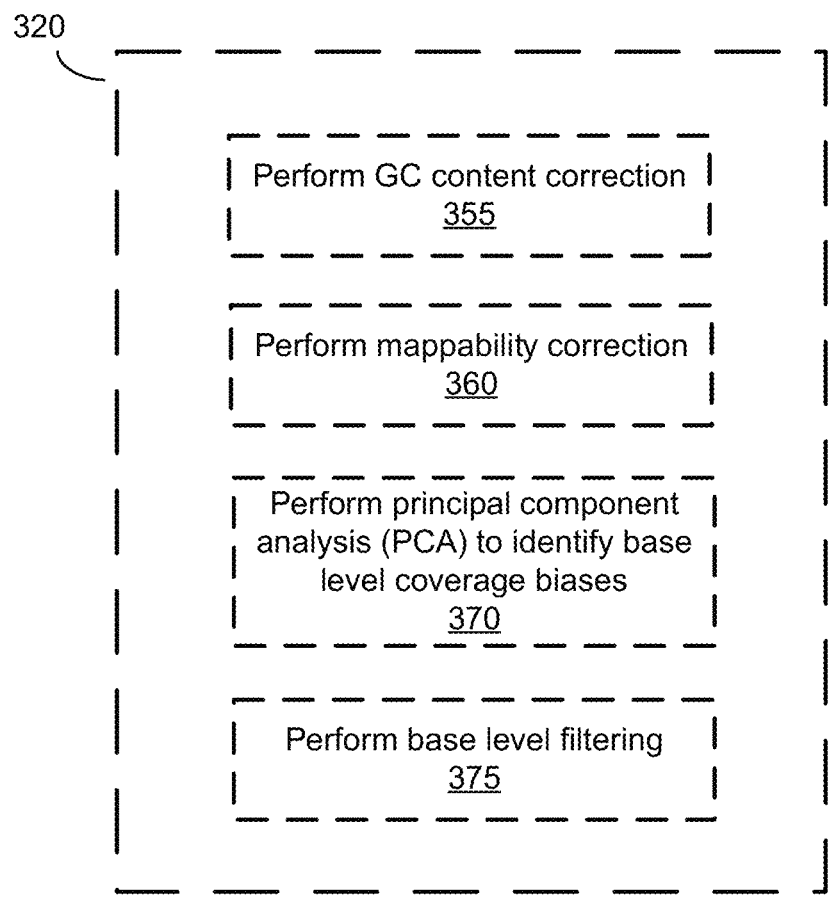
FIG. 3B depicts additional steps for correcting biases that exist at each base position, in accordance with an embodiment.

At step 320, an optional step of correcting for biases at each base position can be performed. Reference is now made to FIG. 3B, which depicts additional steps for correcting biases that arise at each base position, in accordance with an embodiment. Each of the additional steps of performing GC content correction 355, performing mappability correction 360, performing principal component analysis (PCA) 370, and performing base level filtering 375 can be performed independent of another additional correction step. For example, each of steps 355-375 can be performed in different orders. In various embodiments, all of steps 355-375 are performed for a sample to correct for biases that may exist at each base position. In various embodiments, a subset of steps 355-375 can be performed for a sample to correct for a subset of biases that may exist at each base position.

At step 355, the step of performing a GC content correction includes the application of the GC content model. For a base position, a window of the region of the gene is identified. The base position is centered within the window. As stated above, in various embodiments, the window of the region of the gene can range from 4 to 200 base pairs, 5 to 100 base pairs, 6 to 80 base pairs, 8 to 60 base pairs, 10 to 40 base pairs, or 12 to 30 base pairs in size. In various embodiments, the window of the region of the gene is at least 5 base pairs, 10 base pairs, 15 base pairs, 20 base pairs, 25 base pairs, 30 base pairs, 35 base pairs, or 40 base pairs in size. In particular embodiments, the window of the region of the gene is 21 base pairs.

The GC content of the base positions within the window of the region of the gene is provided as input to the GC content model. The GC content model smoothes the GC content across the window of the region of the gene by creating an approximating function. In one embodiment, the GC content model performs a local polynomial regression (LOESS) curve fitting to smooth the GC content across the window. Using the approximated smoothed function, the GC content model outputs a GC content value for the window. To determine whether an additional GC correction is needed, the GC content value for the window is compared to a GC content value for the window that was calculated using the prior training examples. In other words, the GC content value for the window of the test sample is compared to a baseline value to determine whether the GC content from the test sample significantly differs from prior healthy samples. If the GC content value differs significantly in comparison to the baseline, an additional GC correction is performed on the scaled base level coverage $s^d(i)$ determined for the base position. As an example, the scaled base level coverage $s^d(i)$ for the base position can be normalized to the GC content of the window in the target sample. As a specific example, if the GC content of the window for the test sample is a first value whereas the GC content of the window for prior training data is a lower value, the scaled base level coverage $s^d(i)$ can be modified by a factor representing the increase in GC content in the test sample. This accounts for the less efficient pull down of probes due to the higher, or lower, GC content in the targeted nucleic acid region.

At step 360, performing a mappability correction for a base position includes the application of the mappability model. For a base position, a window of the region of the gene is identified. The base position is centered within the window. As stated above, in various embodiments, the window of the region of the gene can range from 4 to 200 base pairs, 5 to 100 base pairs, 6 to 80 base pairs, 8 to 60 base pairs, 10 to 40 base pairs, or 12 to 30 base pairs in size. In various embodiments, the window of the region of the gene is at least 5 base pairs, 10 base pairs, 15 base pairs, 20 base pairs, 25 base pairs, 30 base pairs, 35 base pairs, or 40 base pairs in size. In particular embodiments, the window of the region of the gene is 21 base pairs.

The mappability at each base position of the window of the region of the gene is identified and provided as input to the mappability model. The mappability model smoothes the mappability values of base positions across the window of the region of the gene by creating an approximated smoothed function. In one embodiment, the mappability model performs a local polynomial regression (LOESS) curve fitting to smooth the mappability of base positions across the window. The mappability model outputs a mappability value for the base position given the approximated smoothed function. To determine whether an additional mappability correction is needed, the mappability value for the base position is compared to a mappability value for the base position that was calculated using the prior training examples. In other words, the mappability value for the base position of the test sample is compared to a baseline value to determine whether the mappability value of the base position from the test sample significantly differs from the mappability of the base position from prior healthy samples. If the mappability value differs significantly to the baseline, an additional mappability correction is performed. As an example, the scaled base level coverage $s^d(i)$ for the base position can be normalized relative to the mappability of the base position in the target sample.

At step 370, the principal component analysis model is applied to determine whether an additional PCA correction is needed to account for unknown biases. For each base position, the base level coverage is provided as input to the PCA model, which determines principal components of the base level coverage. The principal components of the base level coverage are compared to baseline principal components determined using training examples. If the differences between the principal components of the base level coverage differ significantly from the baseline principal components determined using training examples, an additional PCA correction can be performed on the base level coverage $s^d(i)$ to eliminate additional unknown biases that may be present.

At step 375, base level filtering for each base position can be performed. Base level filtering can be used to remove base positions that are significant outliers prior to calculating gene level coverage summary (e.g., calculating gene coefficients). For example, for each base position, the standard deviation of base level coverages derived from prior training examples can be used to filter out base positions that significantly deviate from the prior training examples. In one embodiment, base positions that possess a base level coverage that differs by at least a threshold amount from the median base coverage m(i) for the base position can be filtered out. In one embodiment, the threshold amount is a factor multiplied by the standard deviation var(i) of base level coverages derived from prior training examples. In one embodiment, the threshold amount is three times the standard deviation var(i) of base level coverages derived from prior training examples.

Returning to FIG. 3A, at step 325, the coverage level for a gene is estimated based on the base level coverage across the base positions of the gene. Although the subsequent description refers to the coverage level for a gene, in various embodiments, the base level coverage across various base positions can be used to determine a level of coverage for a region (e.g., a region coefficient) of the gene. Thus, the region of the gene can be evaluated to determine whether a CNV for the region exists.

In one embodiment, the base level coverage can be the scaled base level coverage $s^d(i)$ determined after step 315 without further corrections (e.g., Step 320). In other embodiments, the base level coverage can be the corrected base level coverage determined after performing additional corrections (e.g., Step 320). The base level coverage of each base position used to calculate gene level coverage at step 325 is hereafter denoted as $f^d(i)$.

To calculate the coverage level for a gene, the base level coverage of base positions $f^d(i)$ of the gene are applied as input to the gene level model. The gene level model outputs a gene coefficient, which represents a gene level fold change that can likely be attributed to the presence of a CNV. As stated above, the gene level model can be a robust linear model that describes a relationship between the base level coverage and base positions of the gene. The robust linear model can be expressed as:

$$f^d(i)=a+m*i+\text{error} \qquad (9)$$

where m is the gene coefficient outputted by the gene level model, and a is the trained parameter of the gene level model. Given that the gene level model is performing a linear fit across base level coverage across base positions that have been scaled and/or normalized to eliminate forms of bias, the linear fit would theoretically yield a gene coefficient of approximately 1.0 if no CNVs of the gene are present. The gene coefficient represents a gene fold change and can be compared to a pre-determined threshold value. In one embodiment, the pre-determined threshold value is dependent on instrumentation sensitivity to avoid calling a CNV that may arise due to noise. In one embodiment, the pre-determined threshold value is different for each gene of a targeted panel.

As one example, a pre-determined threshold can be a percentage deviancy from the theoretical gene coefficient of 1.0. As an example, a pre-determined threshold can be an 8% deviancy, which leads to an absolute threshold value of 0.92 or 1.08. If the gene coefficient is less than 0.92, a CNV in the form of a deletion of a region of the gene may be present. Alternatively, if the gene coefficient greater than 1.08, a CNV in the form of a duplication of a region of the gene may be present. Based on the comparison between the gene coefficient and the pre-determined threshold value, a CNV for the gene can be identified.

In various embodiments, CNVs are detected for a targeted panel of genes. As an example, the targeted panel may include 100, 200, 500, or more genes such that a gene level model performs the analysis and determines a gene coefficient representing a gene fold change for each gene in the targeted gene panel. Examples of estimated coverage level for a gene (determined as gene level fold change) are described in further detail below with reference to FIGS. 9A, 9B, 9C, 10A, and 10B.

Optionally, at step 330, instead of directly comparing the gene coefficient to a pre-determined threshold value for the purposes of calling a CNV, the gene coefficient (or in various embodiments, a region coefficient) can be standardized by calculating a standard score, which can be used to call a CNV. An example of a standard score can be any one of a z-score, normal score, t-score, or standardized variable. In various embodiments, the gene coefficient is standardized using gene coefficients $g_t$ and a variance $var_t$ of the gene coefficients previously determined using prior training examples derived from various healthy individuals. For example, a z-score can be calculated as:

$$Z \text{ score} = \frac{g - g_t}{var_t} \qquad (10)$$

where g is the gene coefficient determined at step 325. By standardizing the gene coefficient to a standardized score, base level coverage for base positions within the gene that are highly variable can be standardized to reduce the impact of the variability.

Here, the standardized score can be compared to a threshold value to determine whether a CNV is called. The threshold value can be a score dependent on a confidence interval, such as a 90%, 95%, or 99% confidence interval. Therefore, if the standardized score derived from the gene coefficient is larger than the threshold score, a CNV can be called. Conversely, if the standardized score derived from the gene coefficient is less than the threshold score, a CNV is not called.

Computer Implementation

The methods described above, including the method of calling a CNV or detecting presence of cancer in a subject are, in various embodiments, performed on a computer, such as computing device 155 shown in FIG. 1A.

The methods described above can be implemented as computer programs executing on programmable computers that include a processor, a data storage system (including volatile and non-volatile memory and/or storage elements), a graphics adapter, a pointing device, a network adapter, at least one input device, and at least one output device. An output device, such as a display, can be coupled to the graphics adapter. Program code is applied to input data to perform the functions described above and generate output information. The computer can be, for example, a personal computer, microcomputer, or workstation of conventional design.

As one example, the methods depicted in FIGS. 2, 3A, and 3B can be embodied as computer instructions stored on a computer-readable storage medium. The computer instructions, when executed by a processor of a computer, such as computing device 155 shown in FIG. 1A, cause the processor to perform the steps of the methods shown in FIGS. 2, 3A and 3B as described above. In various embodiments, the methods of generating the models (e.g., base level model, base coverage correction models, gene level model, gene coverage correction model) includes the step of storing the parameters of each model. The parameters of each model can be stored on the computer-readable medium for subsequent retrieval during deployment when one or more of the models are applied to call a CNV in a test sample obtained from a subject. In various embodiments, in lieu of generating the models, as shown in FIG. 2, a computer-readable medium that includes the parameters of each model can be received from a third party that generates the models. The parameters of the models can be retrieved and subsequently used to call a CNV in a test sample.

In one embodiment, a machine-readable storage medium includes machine readable data which, when using a computing device programmed with instructions for using the data, causes the computing device to display results. Example results can include an indication of the existence of a CNV in one or more genes. Such results can be used for a variety of purposes, such as patient monitoring, treatment considerations, and the like.

Kit Implementation

Also disclosed herein are kits performing the methods described above, including the method of calling a CNV or detecting a presence of cancer in a subject. Such kits can include reagents for isolating nucleic acids from a test sample. The reagents can further include reagents for sequencing the nucleic acids including buffers and detection agents.

A kit can further include instructions for use of the reagents included in the kit. For example, a kit can include instructions for extracting the nucleic acid from the test sample. Example instructions can be the order in which reagents are to be added, centrifugal speeds to be used to isolate nucleic acids from the test sample, and/or how to operate a hardware device, such as sequencer 145 shown in FIG. 1A, for the purposes of sequencing the nucleic acids of the test sample. In addition to the above components, kits further include instructions of computer software for calling CNVs.

One form in which these instructions can be present is as printed information on a suitable medium or substrate, e.g., a piece or pieces of paper on which the information is printed, in the packaging of the kit, in a package insert. Yet another means would be a computer readable medium, e.g., diskette, CD, hard-drive, network data storage, on which the instructions have been stored in the form of computer code. Yet another means that can be present is a website address which can be used via the internet to access the information at a removed site.

EXAMPLES

Example 1: Theoretical Base Coverage as a Function of Probes

Figure 4:
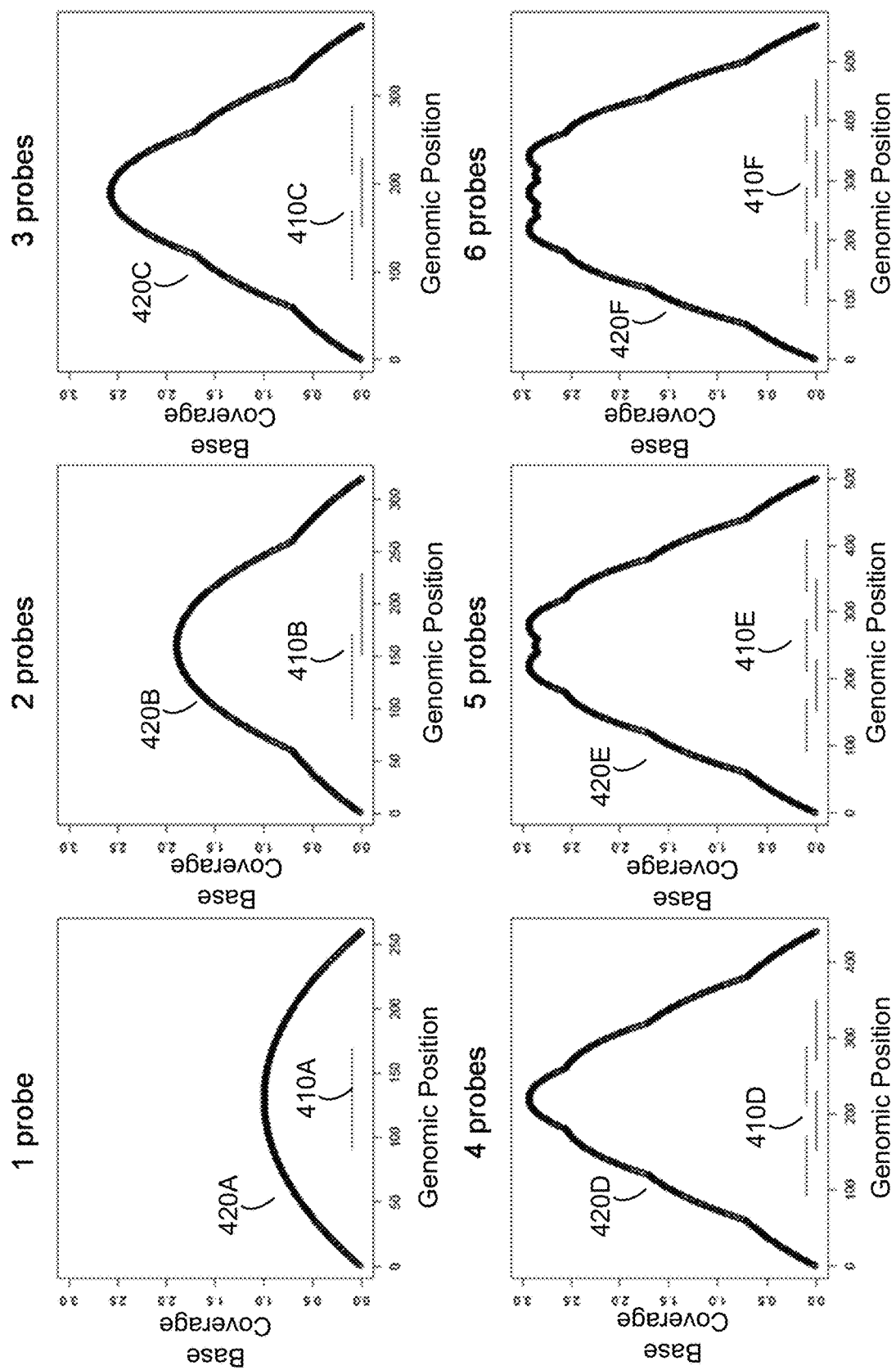
FIG. 4 illustrates a panel of plots of the expected base coverage as a function of the number and location of probes targeting a given region in a cfDNA sample.

FIG. 4 illustrates a panel of plots of the expected base level coverage as a function of the number and location of probes targeting a given region in a cfDNA sample. Generally, for each panel, the base level coverage 420 increases given an increasing number of probes 410. The positions of probes 410 targeting a region are indicated as lines along the genomic position (e.g., x-axis). For a single probe ("1 probe"), a plot of the base coverage 420A is a downward parabola that peaks at about the midpoint of the probe 410A and decreases at base positions further away from the center of the probe 410A. For 2 probes, a plot of the base coverage 420B shows a mixed effect where each probe 410B generates its own coverage of a given region; some base positions will be observed using a first probe, some base positions will be observed using a second probe, and for some base positions there will be a cumulative effect. At genomic positions further away from the center of the probes 410B, the coverage decreases up to a point where the coverage is near zero. This decrease to zero is due to the relatively short range of values for fragments in a cfDNA sample. The average fragment size for a cfDNA sample is about 170 bp with a fragment size range typically from about 50 bp to about 250 bp. Accordingly, a base location that is 300 bases away from a probe will typically not be pulled down with cfDNA fragments pulled down by the probe and the coverage will be zero. For 3 probes, a plot of the base coverage 420C is similar to a plot of the base level coverage 420B for 2 probes except there will be additional areas where there is a mixture of observations generated from each of the 3 probes. Further away from the probes, the coverage will decrease up to a point where the coverage will be zero.

Regions targeted with a low number of probes (≤4 for this example) have an average base level coverage that increases with the number of targeting probes. As the number of targeting probes is further increased (e.g., 5 or 6 probes), the base level coverage (e.g., 420D, 420E, and 420F) plateaus and is relatively constant.

Example 2: Theoretical Base Coverage Across a Targeted Gene

Figure 5:
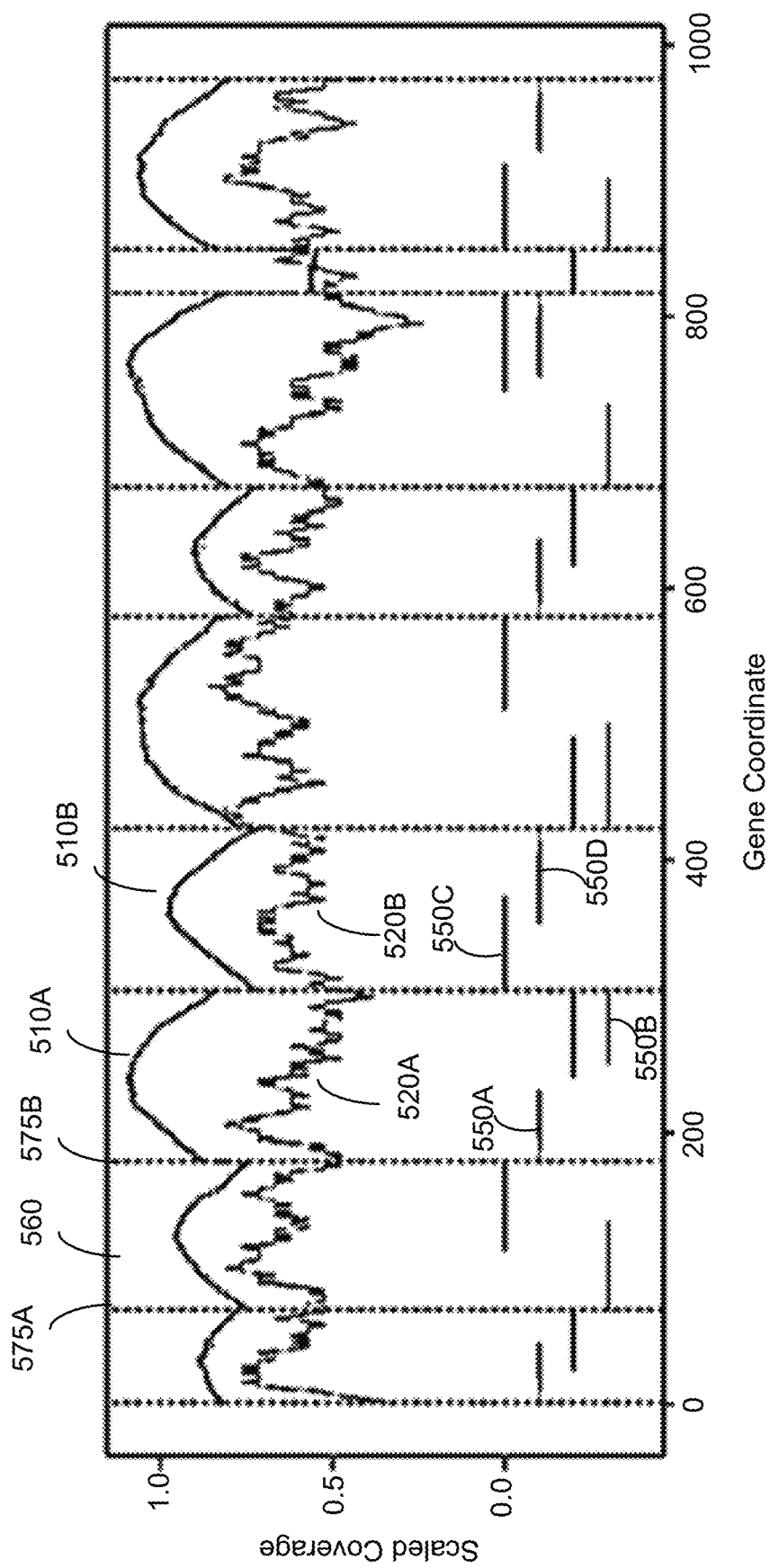
FIG. 5 is a plot showing the observed scaled base coverage for the TNSFRSF14 gene of a cfDNA sample.

FIG. 5 is a plot showing the observed scaled base coverage for the TNSFRSF14 gene of a cfDNA sample. The scaled base coverage at each base position of the gene, which is represented in FIG. 5 as the gene coordinate (e.g., x-axis), is determined by scaling the base level coverage observed at each base position by the median base level coverage observed across the sample.

Each vertical, dotted line 575A and 575B delineates a region 560 of the TNSFRSF14 gene from a different region. In this example, each region 560 of the gene refers to an exon region whereas intron regions of the gene are not shown. Within each exon region 560 of the gene, the probes 550 for the region 560 are depicted as a horizontal line, which indicates the position of each probe 550 within the region 560 of the gene. Here, the probes 560 selected for this analysis were probes used for detection of pancreatic cancer. As shown in FIG. 5, the observed scaled base coverage 510 for each region generally exhibits a downward parabolic shape, as was described above with reference to FIG. 4. The data shows that for regions 560 targeted by 3 probes, the amplitude of the scaled base coverage 510 is higher compared to a lower amplitude of the scaled base coverage for regions targeted by 2 probes. Although not shown, the parabolic shape of the scaled coverage observe for the TNFRSF14 gene is also observed for other targeted genes (data not shown). Also depicted in FIG. 5 is the GC content 520 within each region of the TNFRSF14 gene.

Figure 6:
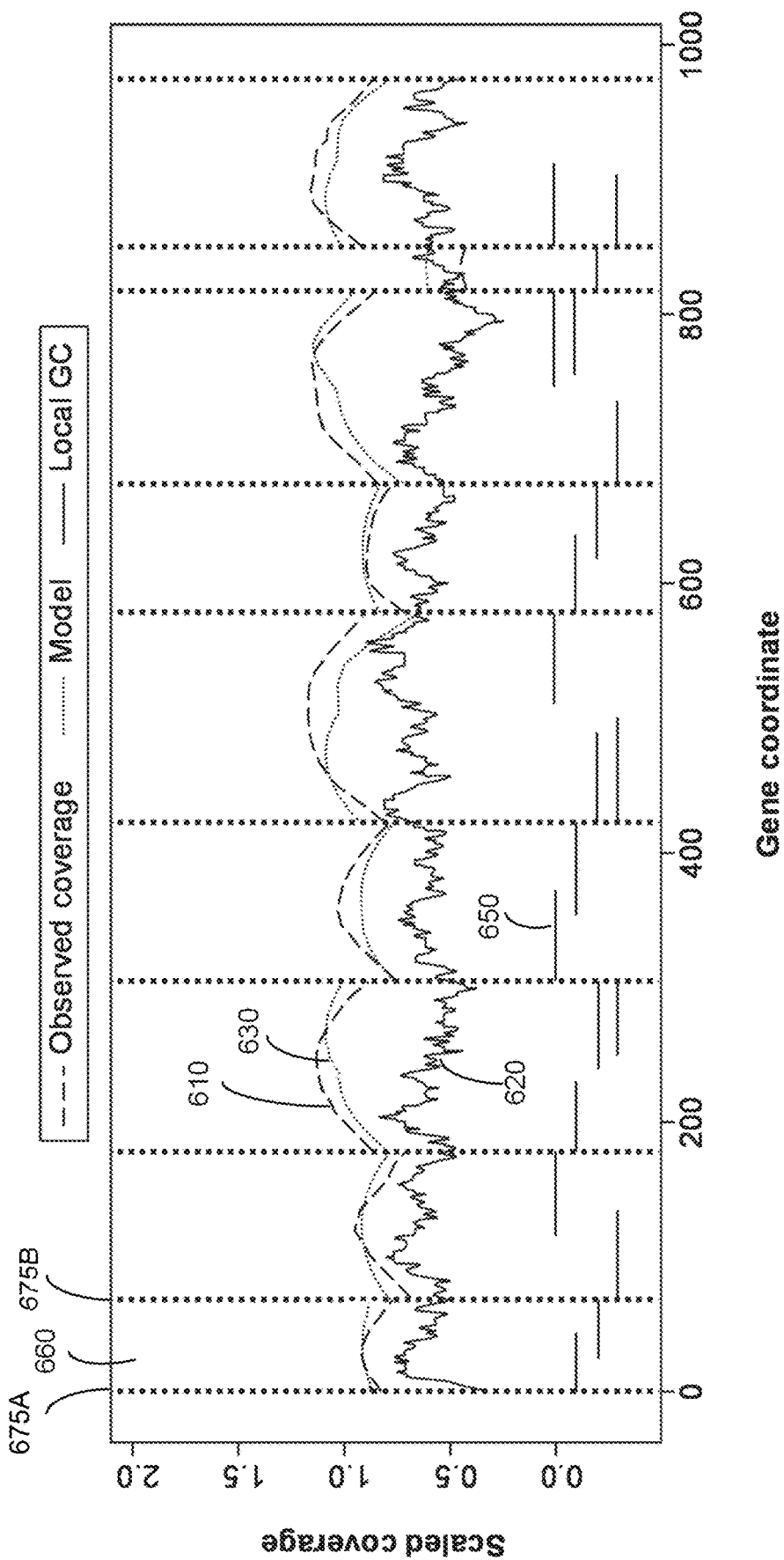
FIG. 6 is a plot showing the observed scaled base coverage versus scaled base coverage predicted by a model using theoretically determined coefficients for the TNFRSF14 gene in the cfDNA sample of FIG. 5.

FIG. 6 is a plot showing the observed scaled base coverage 610 versus scaled base coverage predicted by the base level model 630 using theoretically determined parameters for TNFRSF14 gene in the cfDNA sample of FIG. 4. Similar to FIG. 5, the vertical dotted lines 675A and 675B each delineates a region 660 of the TNSFRSF14 gene from a different region. Within each region 660 of the gene, the probes 650 for the region 660 are depicted as a horizontal line, which indicates the position of each probe 650 within the region 660 of the gene.

To evaluate the model for estimating the theoretical base level coverage, values for the coefficients α and β were selected. Specifically, α=1 and $$\beta = \frac{1}{\left(170 - overhang + \frac{probesize}{2}\right)^2}.$$

The value for β was chosen such that if 3 probes are used, the base level coverage is 1.

The theoretical base level coverage generated by the model is based on two sets of information: the values for α and β and the locations of each of the probes. The data shows that the theoretical base level coverage 630 for each region 660 of the gene approximates the observed base coverage 610 for each region 660 of the gene. In this example, the difference between the observed base level coverage 610 and theoretical base level coverage 630 is likely due to the theoretical choice of the values for the coefficients α and β.

Example 3: Base Level Coverage Determined by Applying the Base Level Model

Figure 7:
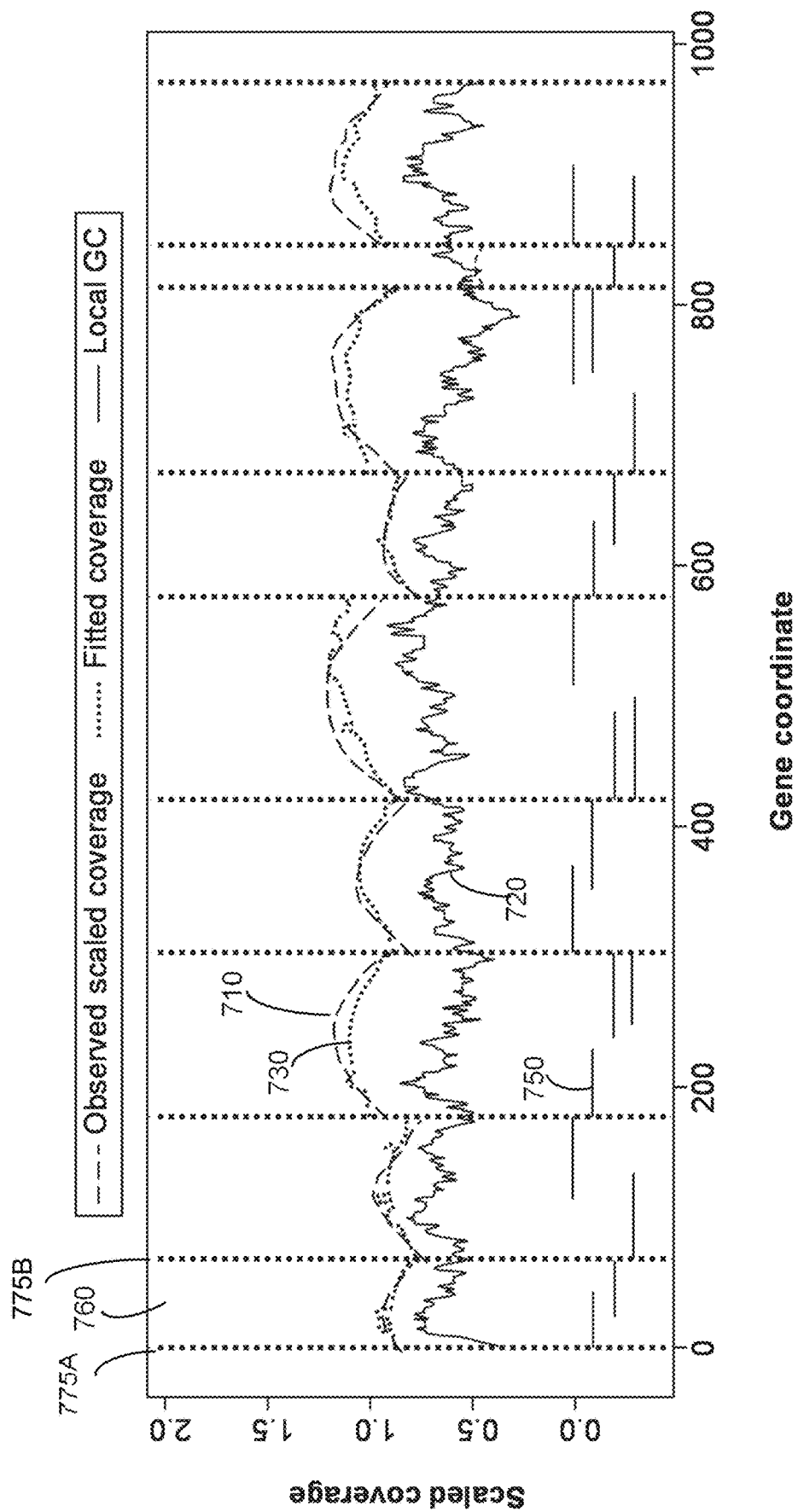
FIG. 7 is a plot showing the observed scaled base coverage versus scaled base coverage predicted by a model using fitted parameters for the TNFRSF14 gene in the cfDNA sample of FIG. 5.

FIG. 7 is a plot showing the observed scaled base coverage versus scaled base coverage predicted by a model using parameters derived from training data for the TNFRSF14 gene in the cfDNA sample of FIG. 6. Similar to FIGS. 5 and 6, the vertical dotted lines 775A and 775B each delineates a region 760 of the TNSFRSF14 gene from a different region. Within each region 760 of the gene, the probes 750 for the region 760 are depicted as a horizontal line, which indicates the location of each probe 750 within the region 760 of the gene with respect to the gene coordinate (e.g., x-coordinate).

For each region of the TNFRSF14 gene, training data including training sequence reads sequenced from a test sample obtained from healthy individuals were used to generate parameters for the base level model (e.g., parameters x and y as described above). Thus, a unique set of parameters for the base level model is generated for each region of the TNFRSF14 gene. To determine the predicted base level coverage 730 for each region of the gene, the parameter x and y for the base level model for each region were used. The predicted base level coverage 730 represents the scaled base level coverage obtained after performing the coverage correction to account for characteristics of hybridization probes (e.g., step 315 in FIG. 3).

The predicted scaled base level coverage 730 closely tracks the observed scaled base coverage 710 for each region 760 of the gene. This establishes that the base level model, and the parameters x and y of the base level model, are useful for modeling the base level coverage across base positions of regions 760 of the gene.

Figure 8:
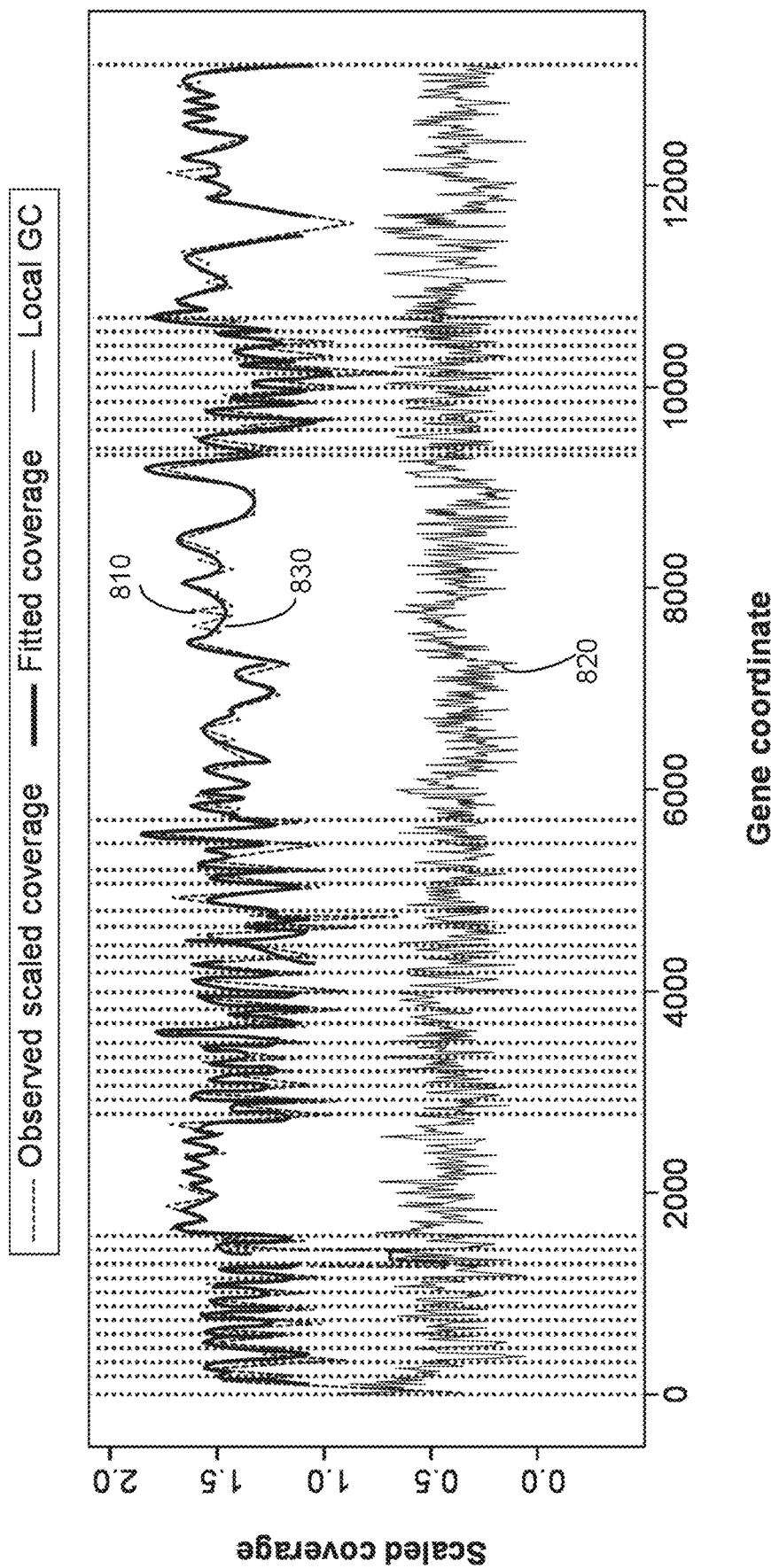
FIG. 8 is a plot showing the observed scaled base coverage versus the fitted coverage for the MET gene in a genomic DNA sample.

Example 4: Determining Gene Level Coverage for Identifying Copy Number Variations FIG. 8 is a plot showing the observed scaled base coverage 810 versus the predicted base level coverage 830 for the MET gene in a genomic DNA sample. The genomic DNA sample was prepared by titrating (spiking-in) genomic DNA from a cell line with an amplification of the MET gene into a genomic DNA sample from another cell line with 2 copies of the MET gene. The proportion of the spike-in reflects how much amplification is expected for the MET gene. In this example, the expected amplification for MET is 1.4× fold change.

For each region of the MET gene, training data including sequence reads sequenced from a test sample obtained from healthy individuals were used to generate parameters for the base level model (e.g., parameters x and y as described above). The scaled base level coverage 830 predicted by the base level model at each base position across various regions of the MET gene closely tracks the observed base level coverage 810 at each base position. This validates the parameters for the base level model. Additionally, as shown in FIG. 8, the amplitudes (measured on the y-axis) of both the observed base level coverage 810 and the scaled base level coverage 830 are in concordance with the expected amplification of 1.4× fold change.

Additional genomic DNA samples were prepared by titrating (spiking-in) genomic DNA from a cell line with amplification of the MET gene into a genomic DNA sample from another cell line with 2 copies of the MET gene. In addition to the aforementioned genomic DNA sample with an expected 1.4× amplification of MET, genomic DNA samples with expected 1.18× and 1.08× amplifications of MET were also prepared. Although not shown, the predicted scaled base level coverage for each of the genomic DNA samples with expected 1.18× and 1.08× amplifications also tracked closely to the observed base level coverage.

For each genomic DNA sample with an expected amplification (e.g., 1.4×, 1.18×, and 1.08×), the scaled base level coverage (e.g., 830 shown in FIG. 8) across the base positions of the MET gene were applied as input to the gene level model, which is a robust linear model (e.g., Equation (9)) that outputs a MET gene coefficient. The gene coefficient for each genomic DNA sample represents the estimated gene fold change of the MET gene in the sample.

Figure 9A:
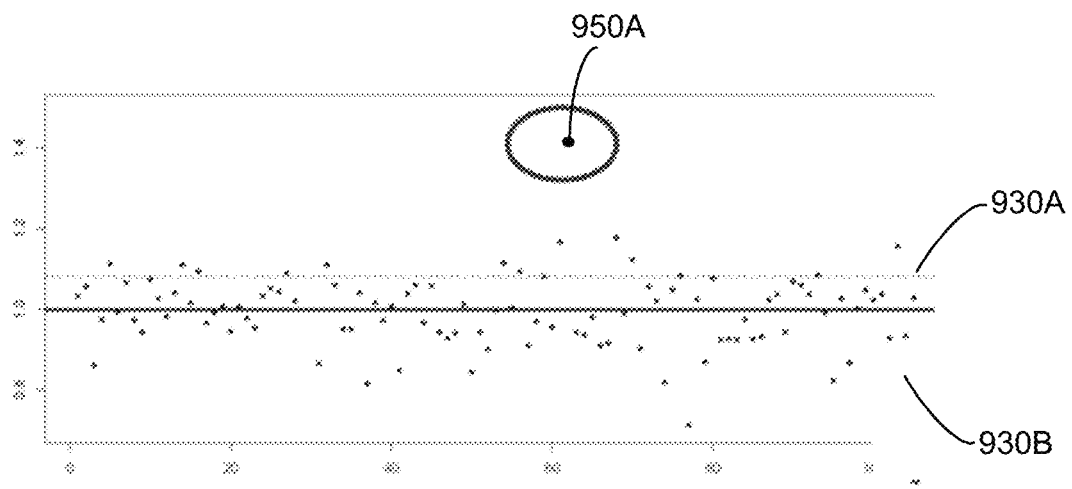
FIG. 9A is a plot showing the estimated gene fold change in a genomic DNA sample with an expected 1.4× amplification of the MET gene.

FIG. 9A is a plot showing the estimated gene fold change in a genomic DNA sample with an expected 1.4× amplification of the MET gene. Each dot in the plot represents a gene with a copy number of 2. Here, the parameter a of the gene level model is previously determined based on training data that includes sequence reads sequenced from samples obtained from healthy individuals. As shown in FIG. 9A, the MET gene coefficient 950A predicted by the gene level model exhibits a 1.4× amplification and is in concordance with the expected results.

For each of the additional genes in the targeted gene panel, a similar analysis was conducted to determine a gene coefficient for the additional gene. Training data including sequence reads derived from healthy individuals were used to generate the parameter (e.g., parameter a) for a robust linear model for the additional gene. Given the parameter for the robust linear model for the additional gene, the scaled base level coverage across regions of each additional gene is applied as input to the gene level model to determine the gene coefficient for the additional gene. As shown in FIG. 9A, a large majority of gene coefficients for the additional genes fall below a threshold value. Here, the threshold value is set to ensure that gene coefficients above the threshold value 930A or below the threshold value 930B are unlikely to have arisen due to random noise.

Figure 9B:
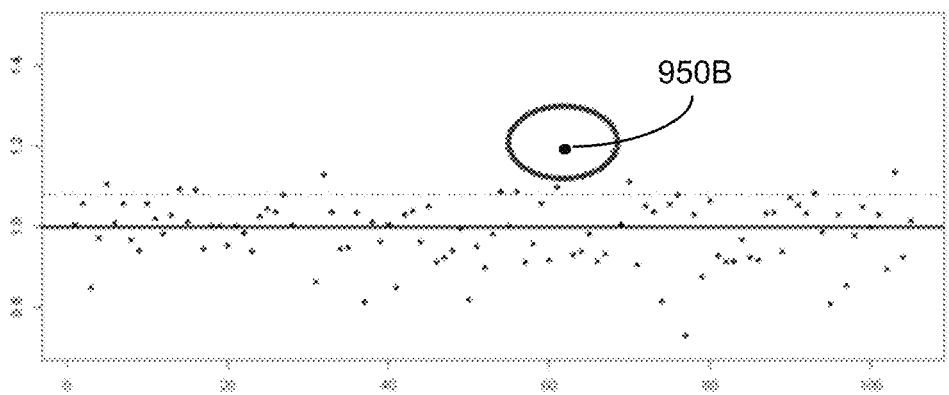
FIG. 9B is a plot showing the estimated gene fold change in a genomic DNA sample with an expected 1.18× amplification of the MET gene.
Figure 9C:
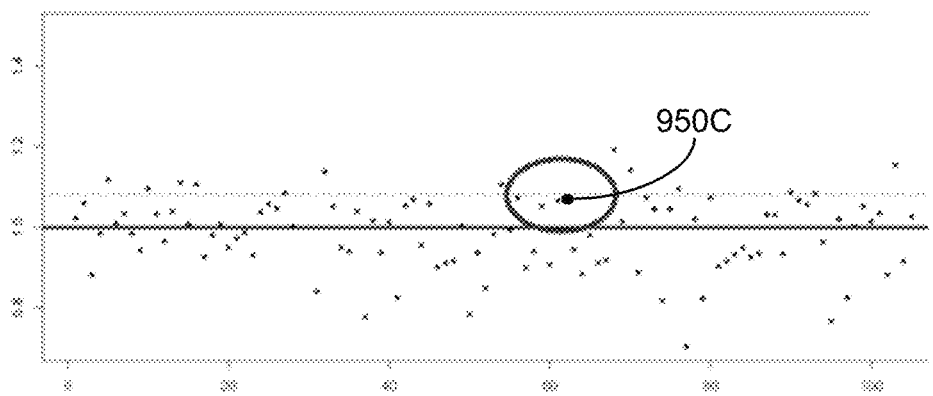
FIG. 9C is a plot showing the estimated gene fold change in a genomic DNA sample with an expected 1.08× amplification of the MET gene.

FIG. 9B is a plot showing the estimated gene fold change in a genomic DNA sample with an expected 1.18× amplification of the MET gene. FIG. 9C is a plot showing the estimated gene fold change in a genomic DNA sample with an expected 1.08× amplification of the MET gene. For each of FIG. 9B and FIG. 9C, the respective MET gene coefficient 950B and 950C is plotted. As shown in FIG. 9B, the MET gene coefficient 950B is approximately 1.18, which aligns with the expected amplification. Similarly, as shown in FIG. 9C, the MET gene coefficient 950C is approximately 1.08, which also aligns with the expected amplification. The data in FIG. 9C establishes that the estimated fold change for the MET gene is concordant with the expected 1.08× amplification for the MET gene; however the level of fold change is within the noise level in the data from additional genes. For the genomic DNA samples, the limit of detection is approximately 1.08× amplification.

Figure 10A:
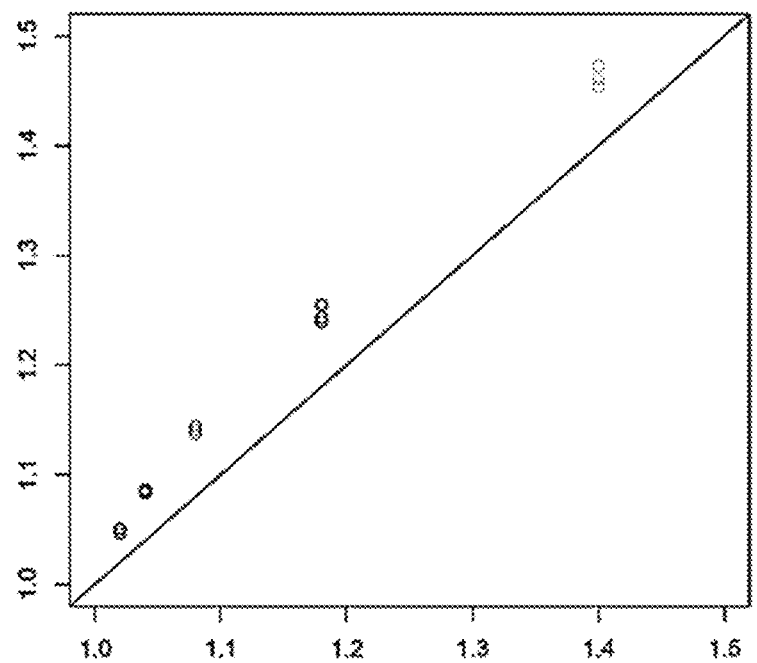
FIG. 10A is a plot showing the relationship between the expected fold change (x-axis) and the estimated fold change (y-axis) for the MET gene in the genomic DNA samples of FIG. 9A-9C.

FIG. 10A is a plot showing the relationship between the expected fold change (x-axis) and the estimated fold change (y-axis) for the MET gene in the genomic DNA samples of FIG. 9A-9C. FIG. 10A is a plot showing the relationship between the expected fold change (x-axis) and the estimated fold change in the fragmented genomic DNA samples (y-axis) for the MET gene. As shown in FIG. 10A, good correlation is observed between the expected fold change and the estimated fold change for MET amplification in the genomic DNA samples.

Figure 10B:
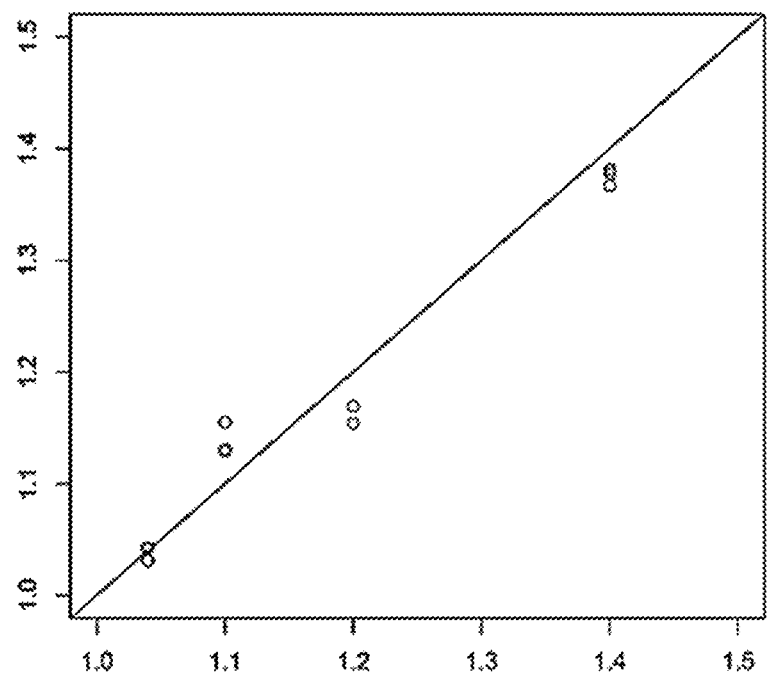
FIG. 10B is a plot showing the relationship between the expected fold change (x-axis) and the fold change (y-axis) for the ERBB2 gene in genomic DNA samples.

FIG. 10B is a plot showing the relationship between the expected fold change (x-axis) and the estimated fold change (y-axis) for the ERBB2 gene in genomic DNA samples. The genomic DNA samples were prepared by titrating (spiking-in) genomic DNA from a cell line with amplification of the ERBB2 gene into a genomic DNA sample from another cell line with 2 copies of the ERBB2 gene. Genomic DNA samples were prepared with expected 1.4×, 1.20×, 1.10×, and 1.04× amplifications of the ERBB2 gene and validated by digital PCR. As shown in FIG. 10B, good correlation is observed between the expected fold change and the estimated fold change for the ERBB2 gene amplification in the genomic DNA samples.

Figure 11:
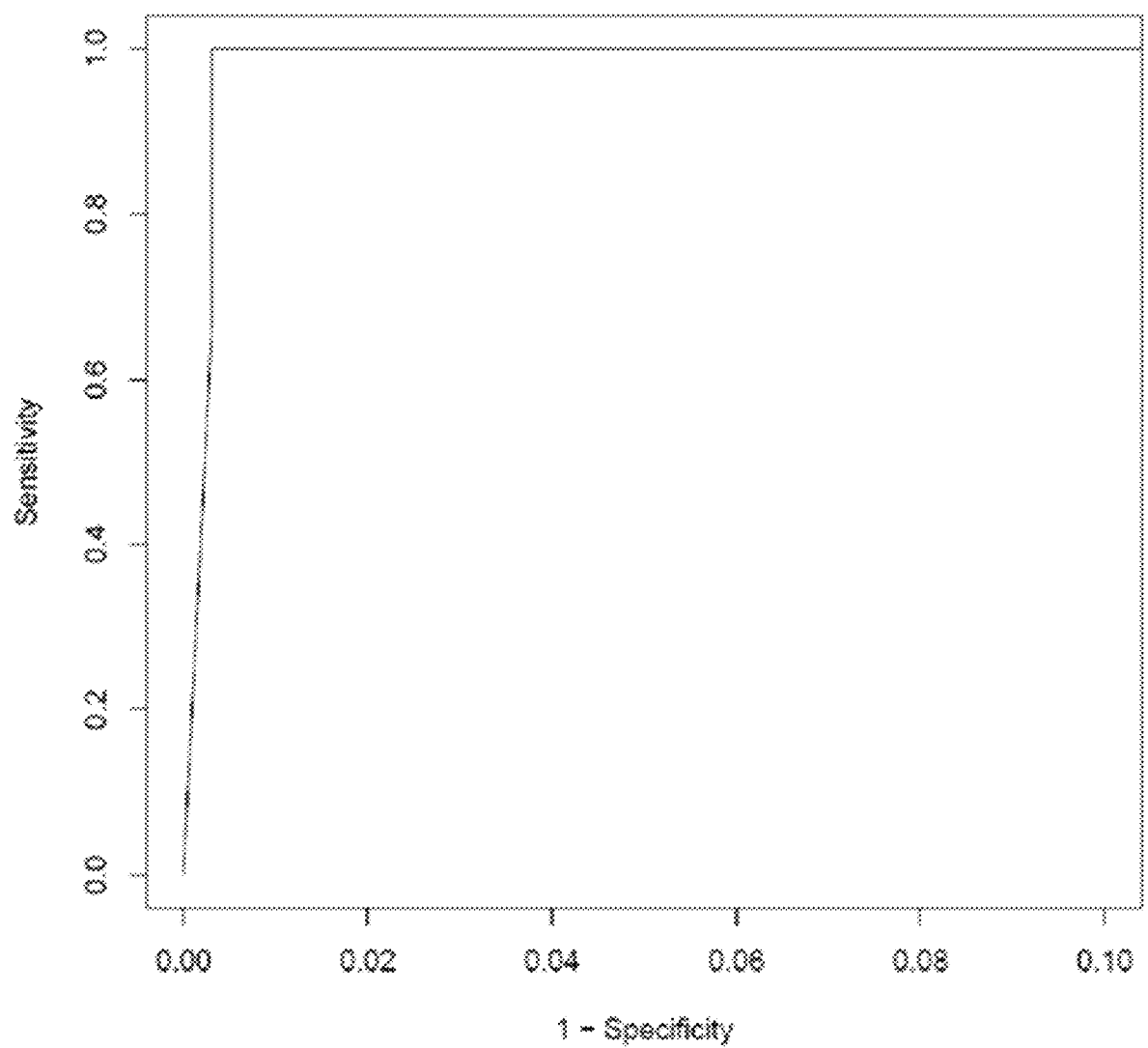
FIG. 11 is a plot showing an ROC curve that indicates the detection of 1.08× amplifications or higher in cfDNA samples.

Example 5: Performance of a Binary Classifier for Calling a Copy Number Variation A binary classifier system was used to call CNVs (i.e., a gene is amplified or it is not amplified) for genes in the targeted panel. Various cutoff points for calling gene amplification can be examined and receiver operating characteristic (ROC) analysis performed. FIG. 11 is a plot showing an ROC curve that indicates detecting 1.08× amplifications or higher in cfDNA samples. The ROC curve was generated using a list of 42 genes known to have CNVs in various types of cancer, measured across 28 samples out of which 12 genes have a 1.08× amplification or higher. Z-scores were generated for all genes and different cut-offs were used for generating the ROC curve.

Additional Considerations

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

What is claimed is:

1. A method for improving detection of cancer by detecting copy number variations indicative of presence of cancer in a cell-free nucleic acid sample, the method comprising:
   modifying the cell-free nucleic acid sample by amplifying fragments in the cell-free nucleic acid sample and enriching the amplified fragments of the cell-free nucleic acid sample using a panel of hybridization probes targeting 500 or more genes, wherein each hybridization probe binds to a portion of a gene;
   performing next generation targeted sequencing on the modified cell-free nucleic acid sample to obtain sequence reads for a plurality of nucleic acid fragments covering the 500 or more genes;
   for each of a plurality of base positions of a gene:
      determining base level coverage of the base position from the sequence reads that cover the base position, and
      scaling the base level coverage of the base position to correct for pull-down efficiency of the hybridization probes, wherein the pull-down efficiency is a rate at which the hybridization probe hybridizes to the portion of the gene and is determined by a level of guanine and cytosine bases in the hybridization probe;
   filtering the plurality of scaled base positions of the gene to generate a filtered set of one or more scaled base positions of the gene, the filtering comprising:
      determining a median coverage level of the gene based on the determined base level coverages of the scaled base positions of the gene, and
      removing scaled base positions of the gene having a base level coverage that differs from the median coverage level beyond a threshold amount to generate the filtered set of the one or more scaled base positions of the gene;

determining a gene coefficient indicating a level of coverage across the gene in the cell-free nucleic acid sample in comparison to a level of coverage of the gene in training samples obtained from healthy individuals based on applying a linear model to one or more modified base level coverages for the filtered set of the one or more scaled base positions of the gene; and detecting the copy number variations indicative of presence of cancer in the cell-free nucleic acid sample based on a comparison of the gene coefficient to a threshold value indicative of a confidence level.

2. The method of claim 1, wherein modifying the base level coverage of the base position comprises applying a first model.

3. The method of claim 2, wherein the first model is generated by:
obtaining training examples comprising training sequence reads that each cross over at least one of the plurality of base positions of a region of the gene;
determining base level coverage for each of the plurality of base positions of the gene based on training sequence reads that cross over the base position of the gene; and
performing one or more fits of base level coverage of the training sequence reads across the plurality of base positions of the gene to obtain one or more parameters of the first model.

4. The method of claim 3, wherein performing one or more fits of base level coverage further comprises:
performing a polynomial fit of base level coverage across the plurality of base positions of the region of the gene to obtain a first set of parameters;
for each base position in the region of the gene, determining a theoretical base level coverage using the first set of parameters; and
generating parameters of the first model by performing a linear fit of theoretical base level coverages across the plurality of base positions of the region of the gene.

5. The method of claim 1, wherein characteristics of a probe used to obtain a nucleic acid fragment comprise a distance between a genomic coordinate of the gene that the probe is centered at and the base position of the gene.

6. The method of claim 1, wherein characteristics of a probe used to obtain a nucleic acid fragment comprise a GC content in the probe.

7. The method of claim 1, wherein scaling the base level coverage of each base position comprises scaling the base level coverage of the base position using a median base coverage level of the sample.

8. The method of claim 1, further comprising:
modifying the base level coverage of the base position by normalizing the base level coverage for GC content within a region of the gene.

9. The method of claim 8, wherein modifying the base level coverage for GC content within the region of the gene comprises performing a fit on GC content within a window of the region of the gene.

10. The method of claim 9, wherein the window of region of the gene is one of between 4 and 200 base pairs in size, between 5 and 100 base pairs in size, between 6 and 80 base pairs in size, between 8 and 60 base pairs in size, between 10 and 40 base pairs in size, or between 12 and 30 base pairs in size.

11. The method of claim 9, wherein the window of the region of the gene is one of at least 5 base pairs in size, at least 10 base pairs in size, at least 15 base pairs in size, at least 20 base pairs in size, at least 25 base pairs in size, at least 30 base pairs in size, at least 35 base pairs in size, or at least 40 base pairs in size.

12. The method of claim 9, wherein the window of the region of the gene is 21 base pairs in size.

13. The method of claim 1, wherein scaling the base level coverage of each base position comprises normalizing the base level coverage for a mappability bias arising from a mappability of the base position.

14. The method of claim 13, wherein normalizing the base level coverage for the mappability bias comprises performing a fit on mappability of base positions within a window of a region of the gene.

15. The method of claim 1, wherein scaling the base level coverage of each base position comprises performing a principal component analysis to identify biases from unknown sources.

16. The method of claim 15, wherein principal components of the principal component analysis are determined for the base position from training samples.

17. The method of claim 1, wherein the threshold amount is dependent on a coverage level deviation of the gene calculated from the determined base level coverages of base positions of the gene.

18. The method of claim 1, wherein the cell-free nucleic acid sample is enriched for DNA fragments indicative of one or more of the presence or absence of cancer, cancer status, or a cancer classification.

19. The method of claim 1, wherein the cell-free nucleic acid sample is obtained from an individual.

20. The method of claim 19, further comprising:
collecting or having collected the cell-free nucleic acid sample from a blood sample of the individual.

21. The method of claim 1, wherein the gene is included in a targeted gene panel.

22. A system for improving detection of cancer by detecting copy number variations indicative of presence of cancer in a cell-free nucleic acid sample, the system comprising:
a sequencing device configured to:
modify the cell-free nucleic acid sample by amplifying fragments in the cell-free nucleic acid sample and enriching the amplified fragments of the cell-free nucleic acid sample using a panel of hybridization probes targeting 500 or more genes, wherein each hybridization probe binds to a portion of one gene; and
perform next generation targeted sequencing on the modified cell-free nucleic acid sample to obtain sequence reads for a plurality of nucleic acid fragments covering the 500 or more genes; and
a computing device comprising a processor and a memory storing computer program instructions that when executed by the processor cause the processor to:
for each of a plurality of base positions of a gene:
determine base level coverage of the base position from the sequence reads that cover the base position, and
scale the base level coverage of the base position to correct for pull-down efficiency of the hybridization probes, wherein the pull-down efficiency is a rate at which the hybridization probe hybridizes to the portion of the gene and is determined by a level of guanine and cytosine bases in the hybridization probe;
filter the plurality of scaled base positions of the gene to generate a filtered set of one or more scaled base positions of the gene, the filtering comprising:

determining a median coverage level of the gene based on the determined base level coverages of the scaled base positions of the gene, and removing scaled base positions of the gene having a base level coverage that differs from the median coverage level beyond a threshold amount to generate the filtered set of the one or more scaled base positions of the gene;

determine a gene coefficient indicating a level of coverage across the gene in the cell-free nucleic acid sample in comparison to a level of coverage of the gene in training samples obtained from healthy individuals based on applying a linear model to one or more modified base level coverages for the filtered set of the one or more scaled base positions of the gene; and detect the copy number variations indicative of presence of cancer in the cell-free nucleic acid sample based on a comparison of the gene coefficient to a threshold value indicative of a confidence level.

* * * * *